US009764145B2

(12) United States Patent
Callas et al.

(10) Patent No.: US 9,764,145 B2
(45) Date of Patent: Sep. 19, 2017

(54) SYSTEM AND METHOD FOR SYNCHRONIZING ENERGY DELIVERY TO THE CARDIAC RHYTHM

(71) Applicant: AngioDynamics, Inc., Latham, NY (US)

(72) Inventors: Peter Callas, Castro Valley, CA (US); James Lovewell, San Leandro, CA (US); Bradley C. Stribling, Alamo, CA (US); Dave Warden, Belmont, CA (US)

(73) Assignee: AngioDynamics, Inc.

( * ) Notice: Subject to any disclaimer, the term of this patent is extended or adjusted under 35 U.S.C. 154(b) by 0 days.

(21) Appl. No.: 14/529,811

(22) Filed: Oct. 31, 2014

(65) Prior Publication Data

US 2015/0088220 A1 Mar. 26, 2015

Related U.S. Application Data

(63) Continuation of application No. 12/790,681, filed on May 28, 2010, now Pat. No. 8,903,488.

(51) Int. Cl.
*A61N 1/00* (2006.01)
*A61N 1/37* (2006.01)
*A61N 1/365* (2006.01)
*A61N 1/32* (2006.01)

(52) U.S. Cl.
CPC ............ *A61N 1/3706* (2013.01); *A61N 1/365* (2013.01); *A61N 1/3702* (2013.01); *A61N 1/327* (2013.01)

(58) Field of Classification Search
CPC ........ A61B 5/00; A61B 5/0452; A61N 1/368; A61N 1/3956
USPC .................................................. 607/5, 9, 509
See application file for complete search history.

(56) References Cited

U.S. PATENT DOCUMENTS

| 1,653,819 | A | 12/1927 | Ephraim et al. |
| 3,730,238 | A | 5/1973 | Butler |
| 3,746,004 | A | 7/1973 | Jankelson |
| 3,871,359 | A | 3/1975 | Pacela |

(Continued)

FOREIGN PATENT DOCUMENTS

| EP | 2488251 A2 | 8/2012 |
| EP | 2593179 A1 | 5/2013 |

(Continued)

OTHER PUBLICATIONS

International Search Report for PCT-US-10-053077 ISR dated Aug. 2, 2011.

(Continued)

*Primary Examiner* — Nadia A Mahmood
(74) *Attorney, Agent, or Firm* — Peter Flora, Esq.

(57) ABSTRACT

A system for synchronizing application of treatment signals with a cardiac rhythm is provided. The system includes a memory that receives and stores a synchronization signal indicating that a predetermined phase such as R-wave of a cardiac rhythm of a patient has started. A synchronization module analyzes whether the stored synchronization signal is erroneous and if so, prevents a medical treatment device from applying a treatment energy signal such as an IRE pulse to a patient to take into account an irregular heart beat and noise in the synchronization signal in order to maximize safety of the patient.

16 Claims, 22 Drawing Sheets

(56) References Cited

U.S. PATENT DOCUMENTS

| | | |
|---|---|---|
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy, Jr. et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| 5,277,201 A | 1/1994 | Stern |
| 5,279,564 A | 1/1994 | Taylor |
| 5,281,213 A | 1/1994 | Milder et al. |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,417,687 A | 5/1995 | Nardella et al. |
| 5,425,752 A | 6/1995 | Vu'Nguyen |
| 5,439,440 A | 8/1995 | Hofmann |
| 5,439,444 A | 8/1995 | Andersen et al. |
| 5,458,597 A | 10/1995 | Edwards et al. |
| 5,458,625 A | 10/1995 | Kendall |
| 5,462,521 A | 10/1995 | Brucker et al. |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| 5,630,426 A | 5/1997 | Eggers et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,672,174 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,707,332 A | 1/1998 | Weinberger |
| 5,718,246 A | 2/1998 | Vona |
| 5,720,921 A | 2/1998 | Meserol |
| 5,728,143 A | 3/1998 | Gough et al. |
| 5,735,847 A | 4/1998 | Gough et al. |
| 5,752,939 A | 5/1998 | Makoto |
| 5,778,894 A | 7/1998 | Dorogi et al. |
| 5,782,827 A | 7/1998 | Gough et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,810,804 A | 9/1998 | Gough et al. |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,863,290 A | 1/1999 | Gough et al. |
| 5,865,787 A | 2/1999 | Shapland et al. |

(56) References Cited

U.S. PATENT DOCUMENTS

| | | |
|---|---|---|
| 5,866,756 A | 2/1999 | Giros et al. |
| 5,868,708 A | 2/1999 | Hart et al. |
| 5,873,849 A | 2/1999 | Bernard |
| 5,904,648 A | 5/1999 | Arndt et al. |
| 5,913,855 A | 6/1999 | Gough et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,954,745 A | 9/1999 | Gertler et al. |
| 5,957,919 A | 9/1999 | Laufer |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,012,885 A | 1/2000 | Taylor et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| 6,102,885 A | 8/2000 | Bass |
| 6,106,521 A | 8/2000 | Blewett et al. |
| 6,106,524 A | 8/2000 | Eggers et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| 6,233,490 B1 | 5/2001 | Kasevich |
| 6,235,023 B1 | 5/2001 | Lee et al. |
| 6,241,702 B1 | 6/2001 | Lundquist et al. |
| 6,241,725 B1 | 6/2001 | Cosman |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,328,735 B1 | 12/2001 | Curley et al. |
| 6,330,478 B1 | 12/2001 | Lee et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 | 11/2002 | Cosman et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,497,704 B2 | 12/2002 | Ein-Gal |
| 6,500,173 B2 | 12/2002 | Underwood et al. |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| 6,526,320 B2 | 2/2003 | Mitchell |
| 6,530,922 B2 | 3/2003 | Cosman et al. |
| 6,533,784 B2 | 3/2003 | Truckai et al. |
| 6,537,976 B1 | 3/2003 | Gupta |
| 6,558,378 B2 | 5/2003 | Sherman et al. |
| 6,562,604 B2 | 5/2003 | Rubinsky et al. |
| 6,575,967 B1 | 6/2003 | Leveen et al. |
| 6,575,969 B1 | 6/2003 | Rittman, III et al. |
| 6,589,161 B2 | 7/2003 | Corcoran |
| 6,589,174 B1 | 7/2003 | Chopra et al. |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | McCormick et al. |
| 6,616,657 B2 | 9/2003 | Simpson et al. |
| 6,627,421 B1 | 9/2003 | Unger et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,682,501 B1 | 1/2004 | Nelson et al. |
| 6,689,096 B1 | 2/2004 | Loubens et al. |
| 6,689,127 B1 | 2/2004 | Gough et al. |
| 6,692,493 B2 | 2/2004 | McGovern et al. |
| 6,694,979 B2 | 2/2004 | Deem et al. |
| 7,706,865 B1* | 4/2010 | Snell ............... A61N 1/3622 600/509 |
| 2003/0135242 A1* | 7/2003 | Mongeon ............ A61N 1/3956 607/5 |
| 2008/0146934 A1* | 6/2008 | Czygan ............... A61B 8/06 600/453 |

FOREIGN PATENT DOCUMENTS

| | | | |
|---|---|---|---|
| EP | | 2627274 A2 | 8/2013 |
| EP | | 2651505 A1 | 10/2013 |
| ES | | 2300272 T3 | 6/2008 |

(56) References Cited

FOREIGN PATENT DOCUMENTS

| | | |
|---|---|---|
| ES | 2315493 T3 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010511467 A | 4/2010 |
| JP | 2012510332 A | 5/2012 |
| JP | 4252316 B2 | 9/2012 |
| JP | 2012521863 A | 9/2012 |
| KR | 101034682 B1 | 9/2012 |
| WO | WO9104014 A1 | 4/1991 |
| WO | WO9634571 A1 | 11/1996 |
| WO | WO9639531 A1 | 12/1996 |
| WO | WO9810745 A1 | 3/1998 |
| WO | WO9814238 A1 | 4/1998 |
| WO | WO9901076 A1 | 1/1999 |
| WO | WO9904710 A1 | 2/1999 |
| WO | WO0020554 A1 | 4/2000 |
| WO | WO0107583 A1 | 2/2001 |
| WO | WO0107584 A1 | 2/2001 |
| WO | WO0107585 A1 | 2/2001 |
| WO | WO0110319 A1 | 2/2001 |
| WO | WO0148153 A1 | 7/2001 |
| WO | WO0170114 A1 | 9/2001 |
| WO | WO0181533 A1 | 11/2001 |
| WO | WO0200554 A1 | 1/2002 |
| WO | WO02078527 A2 | 10/2002 |
| WO | WO02089686 A1 | 11/2002 |
| WO | WO02100459 A2 | 12/2002 |
| WO | WO03020144 A1 | 3/2003 |
| WO | WO03047684 A2 | 6/2003 |
| WO | WO03099382 A1 | 12/2003 |
| WO | WO2004037341 A2 | 5/2004 |
| WO | WO2004080347 A2 | 5/2004 |
| WO | WO2005065284 A2 | 7/2005 |
| WO | WO2006017666 A2 | 2/2006 |
| WO | WO2006130194 A2 | 12/2006 |
| WO | WO2007067628 A1 | 6/2007 |
| WO | WO2007067937 A2 | 6/2007 |
| WO | WO2007067938 A2 | 6/2007 |
| WO | WO2007067939 A2 | 6/2007 |
| WO | WO2007067940 A2 | 6/2007 |
| WO | WO2007067941 A2 | 6/2007 |
| WO | WO2007067943 A2 | 6/2007 |
| WO | WO2007070361 A2 | 6/2007 |
| WO | WO2007123690 A2 | 11/2007 |
| WO | WO2007137303 A2 | 11/2007 |
| WO | WO2008063195 A1 | 5/2008 |
| WO | WO2008101086 A2 | 8/2008 |
| WO | WO2008101091 A2 | 8/2008 |
| WO | WO2009036468 A1 | 3/2009 |
| WO | WO2009046176 A1 | 4/2009 |
| WO | WO2009134876 A1 | 11/2009 |
| WO | WO2009135070 A1 | 11/2009 |
| WO | WO2009137800 A2 | 11/2009 |
| WO | WO2010064154 A1 | 6/2010 |
| WO | WO2010085765 A2 | 7/2010 |
| WO | WO2010117806 A1 | 10/2010 |
| WO | WO2010118387 A1 | 10/2010 |
| WO | WO2010128373 A1 | 11/2010 |
| WO | WO2010132472 A1 | 11/2010 |
| WO | WO2010151277 A1 | 12/2010 |
| WO | WO2011028937 A1 | 3/2011 |
| WO | WO2011047387 A2 | 4/2011 |
| WO | WO2011062653 A1 | 5/2011 |
| WO | WO2011072221 A1 | 6/2011 |
| WO | WO2011135294 A1 | 11/2011 |
| WO | WO2012006533 A1 | 1/2012 |
| WO | WO2012051433 A2 | 4/2012 |
| WO | WO2012054560 A1 | 4/2012 |
| WO | WO2012054573 A2 | 4/2012 |
| WO | WO2012063266 A2 | 5/2012 |
| WO | WO2012071526 A2 | 5/2012 |
| WO | WO2012088149 A2 | 6/2012 |

OTHER PUBLICATIONS

International Search Report for PCT-US-10-053077 WOSA dated Aug. 2, 2011.
International Search Report for PCT/US2009/042100 IPRP IPRP dated Nov. 2, 2010.
International Search Report for EP 09739678 SESR dated May 3, 2012.
International Search Report for PCT/US2010/029243 IPRP dated Oct. 4, 2011.
International Search Report for PCT/US2009/048270 IPRP dated Jan. 5, 2011.
International Search Report for PCT/US2007/000084 IPRP dated Jul. 8, 2008.
International Search Report for PCT/US2009/042100 ISR dated Jul. 9, 2009.
International Search Report for PCT/US2009/042100 WOSA dated Jul. 9, 2009.
International Search Report for PCT/US2009/048270 ISR dated Feb. 11, 2010.
International Search Report for PCT/US2009/048270 WOSA dated Feb. 11, 2010.
International Search Report PCT/US2009042100 ESO dated May 11, 2012.
International Search Report PCT/US2009/038661 ISR dated Jun. 12, 2009.
International Search Report 12002108.4 ESO dated Jun. 12, 2013.
International Search Report PCT/US07/00084 WOSA dated Dec. 14, 2007.
International Search Report for PCT/US2011/056177 IPRP dated Apr. 16, 2013.
International Search Report for 06751655 SESR dated Oct. 9, 2016.
International Search Report for PCT/US2010/053077 ISR IPRP dated Apr. 17, 2012.
International Search Report for 11833421 SESR dated Mar. 18, 2014.
International Search Report for PCT/US2011/024909 ISR dated Oct. 18, 2011.
International Search Report for PCT/US2011/024909 WOSA dated Oct. 18, 2011.
International Search Report for 07716249 SESR dated Jan. 19, 2009.
International Search Report for PCT/US2009/062806 IPRP dated Jan. 4, 2012.
International Search Report for PCT/US2009/062806 ISR dated Jan. 19, 2010.
International Search Report for PCT/US2009/062806 WOSA dated Jan. 19, 2010.
International Search Report for 10824248.8 ESO dated Jan. 20, 2014.
International Search Report for PCT/US2009/047969 ISR dated Jan. 21, 2010.
International Search Report for PCT/US2009/047969 WOSA dated Jan. 21, 2010.
International Search Report for PCT/US2011/024909 IPRP dated Aug. 21, 2012.
International Search Report for PCT/US2011/025003 IPRP dated Aug. 21, 2012.
International Search Report for PCT/US2009/047969 IPRP dated Dec. 21, 2010.
International Search Report for PCT/US2010/036734 ISR dated Dec. 23, 2010.
International Search Report for PCT/US2010/036734 WOSA dated Dec. 23, 2010.

(56) References Cited

OTHER PUBLICATIONS

International Search Report for PCT/US2011/025003 ISR dated Oct. 24, 2011.
International Search Report for PCT/US2011/025003 WOSA dated Oct. 24, 2011.
International Search Report for PCT/US2011/062067 ISR dated Jul. 25, 2012.
International Search Report for PCT/US2011/062067 WOSA dated Jul. 25, 2012.
International Search Report for PCT/US06/16045 ISR dated Sep. 25, 2007.
International Search Report for PCT/US2010/022011 IPRP dated Jul. 26, 2011.
International Search Reprot for PCT/US2011056177 ESO dated Mar. 28, 2014.
International Search Report for PCT/US2011/062067 IPRP dated May 28, 2013.
International Search Report for PCT/US2009/038661 IPRP dated Sep. 28, 2010.
International Search Report for 06751655.9 ESO dated Oct. 29, 2009.
International Search Report for PCT/US2010/036734 IPRP dated Nov. 29, 2011.
International Search Report for 12002108 EPS dated May 30, 2012.
International Search Report for PCT/US2011/056177 ISR dated May 30, 2012.
International Search Report for PCT/US2011/056177 WOSA dated May 30, 2012.
International Search Report for PCT/US10/29243 ISR dated Jul. 30, 2010.
International Search Report for PCT/US2010/029243 WOSA dated Jul. 30, 2010.
International Search Report for PCT/US2010/022011 ISR dated Aug. 30, 2010.
International Search Report for PCT/US2010/022011 WOSA dated Aug. 30, 2010.
International Search Report for PCT/US2006/016045 IPRP dated Oct. 30, 2007.
Cowley, Lifestyle Good news for boomers, Newsweek, Dec. 30, 1996.
Sharma, et al, Poloxamer 188 decrease susceptibility of artificial lipid membranes to electroporation, Biophysical Journal, 1996, vol. 71, pp. 3229-3241.
Blad, Baldetorp, Impedance spectra of tumour tissue in comparison with normal tissue; a possible clinical application for electrical impedance tomography, Physiol. Meas., 1996, 17, pp. A105-A115.
Ho, Mittal, Electroporation of cell membranes: a review, Critical Reviews in Biotechnology, 1996, 16(4), pp. 349-362.
Gilbert, et al, Rapid report novel electrode designs for electrochemotherapy, Biochimica et Biophysica Acta, Feb. 11, 1997, 1134, pp. 9-14.
Zlotta, et al, Possible mechanisms fo action of transsurethral needle ablation of the prostate on benign prostatic hyperplasia systems: A neurohistochemical study, Journal of Urology, Mar. 1997, vol. 157, No. 3, pp. 894-899.
Duraiswami et al, Solution of electrical impedance tomography equations using boundary element methods, Boundary Element Technology XII, Apr. 1997, pp. 227-237.
Fox, Nicholls, Sampling conductivity images via MCMC, Auckland University, Auckland, New Zealand.
Naslund, Transurethral needle ablation of the prostate, Urology, Aug. 1997, vol. 50, No. 2, pp. 167-172.
Boone, et al, Review imaging with electricity: Report of the European concerted action on impedance tomography, Journal of Medical Engineering & Technology, Nov. 1997, vol. 21, No. 6, pp. 201-232.
Lurquin, Review: Gene transfer by electroporation, Molecular Biotechnology, 1997, vol. 7, pp. 5-31.
Hapala, Breaking the barrier: methods for reversible permeabilization of cellular membranes, Critical Reviews in Biotechnology, 1997, 17(2), pp. 105-122.
Duraiswami, et al, Boundary element techniques for efficient 2-D and 3-D electrical impedance tomography, Chemical Engineering Science, 1997, vol. 52, No. 13, pp. 2185-2196.
Pinero, et al, Apoptotic and necrotic cell death are both induced by electroporation in HL60 human promyeloid leukaemia cells, Apoptosis, 1997, 2, pp. 330-336.
Miklavcic, et al, The importance of electric field distribution for effective in vivo electroporation of tissues, Biophysical Journal, May 1998, vol. 74, pp. 2152-2158.
Issa, et al, Recent Reports: The TUNA procedure for BPH: Review of the technology, Infections in Urology, Jul. 1998.
Lundqvist, et al, Altering the biochemical state of individual cultured cells and organelles with ultramicroelectrodes, Proc. Natl. Acad. Sci. USA, Sep. 1998, Vo. 95, pp. 10356-10360.
Issa, et al, Specialty Surgery: The TUNA procedure for BPH: Basic procedure and clinical results, Infections in Urology, Sep. 1998.
Dev, et al, Sustained local delivery of heparin to the rabbit arterial wall with an electroporation catheter, Catheterization and Cardiovascular Diagnosis, 1998, 45, pp. 337-345.
Duraiswami, et al, Efficient 2D and 3D electrical impedance tomography using dual reciprocity boundary element techniques, Engineering Analysis with Boundary Elements, 1998, 22, pp. 13-31.
Mir, et al, Effective treatment of cutaneous and subcutaneous malignant tumors by electrochemotherapy, 1998, British Journal of Cancer, 77 (12), pp. 2336-2342.
Sersa, et al, Tumor blood flow modifying effect of electrochemotherapy with Bleomycin, Anticancer Research, 1999, 19, pp. 4017-4022.
Thompson, et al, To determine whether the temperature of 2% lignocaine gel affects the initial discomfort which may be associated with its instillation into the male urethra, BJU International, 1999, 84, pp. 1035-1037.
Gumerov, et al, The dipole approximation method and its coupling with the regular boundar yelement method for efficient electrical impedance tomography, BETECH 99.
Yang, et al, Dielectric properties of human luekocyte subpopulations determined by electrorotation as a cell separation criterion, Jun. 1999, vol. 76, pp. 3307-3014.
Huang, Rubinsky, Micro-electroporation: improving the efficiency and understanding of electrical permeabilization of cells, Biomedical Microdevices, 1999, 2:2, pp. 145-150.
Mir, Orlowski, Mechanisms of electrochemotherapy, Advanced Drug Delivery Reviews, 1999, 35, pp. 107-118.
Jaroszeski, et al, In vivo gene delivery by electroporationi, Advanced Drug Delivery Reviews, 1999, 35, pp. 131-137.
Gehl, et al, In vivo electroporation of skeletal muscle: threshold, efficacy and relation to electric field distribution, Biochimica et Biophysica Acta, 1999, 1428, pp. 233-240.
Heller, et al, Clinical applications of electrochemotherapy, Advanced Drug Delivery Reviews, 1999, 35, 119-129.
Holder, et al, Low-Frequency System, Assessment and calibration of a low-frequency impedance tomography (EIT), optimized for use in imaging brain function in ambulant human subjects, Annals New York Academy Sciences, pp. 512-519.
Dev, et al, Medical applications of electroporation, IEEE Transactions on Plasma Science, Feb. 2000, vol. 28, No. 1, pp. 206-222.
Ivanusa, et al, MRI macromolecular contrast agents as indicators of changed tumor blood flow, Radiol Oncol, 2001, 35, 2, pp. 139-147.
Ermolina, et al, Study of normal and malignant white blood cells by time domain dielectric spectroscopy, IEEE Transactions on Dielectrics and Electrical Insulation, Apr. 2001, vol. 8, No. 2, pp. 253-261.
Carson, et al, Improving patient satisfaction, BPH management strategies, Supplement to Urology Times, May 2001, Vo. 29, Suppl. 1, pp. 1-22.
Beebe, et al, Nanosecond pulsed electric field (nsPEF) effects on cells and tissues: Apoptosis induction and tumor growth inhibition, IEEE, 2002, pp. 211-215.
N/A, When patient satisfaction is your goal, Precision Office TUNA System, VidaMed, Inc.

(56) References Cited

OTHER PUBLICATIONS

Chandrasekar, et al, Transurethral needle ablation of the prostate (TUNA)—A prospective study, six year follow up, pp. 1210.

N/A, Highlights from worldwide clinical studies, Transurethral needle ablation (TUNA), Vidamed's Office TUNA System, VidaMed, Inc. , pp. 1-4.

Schoenbach, et al, Intracellular effect of ultrashort electrical pulses, Bioelectromagnetics, 2001, 22, pp. 440-448.

Cemazar, et al, Electroporation of human microvascular endothelial cells: evidence for an anti-vascular mechanism of electrochemotherapy, British Journal of Cancer, 2001, 84, 4, pp. 565-570.

Kotnik, et al, Cell membrane electropermeabilization by symmetrical biopolar rectangular pulses, Part I. Increased efficiency of permeabilization, Bioelectrochemistry, 2001, 54, pp. 83-90.

Kotnik, et al, Cell membrane electropermeabilization by symmetrical biopolar rectangular pulses, Part II. Reduced electrolytic contamination, Bioelectrochemistry, 2001, 54, pp. 91-95.

Lebar, Miklavcic, Cell electropermeabilization to small molecules in vitro: control by pulse parameters, Radiol Oncol, 2001, 35, 3, pp. 193-202.

Naslund, Cost-effectiveness of minimally invasive treatments and transurethral resection (TURP) in benign prostatic hyperplasia (BPH), Unveristy of Maryland School of Medicine, 2001, pp. 1213.

Davalos, et al, A feasibility study for electrical impedance tomography as a means to montior tissue electroporatioin for molecular medicien, IEEE Transactions on Biomedical Engineering, Apr. 2002, vol. 49, No. 4, pp. 400-403.

Jossinet, et al, Electrical impedance end-tomography: Imaging tissue from inside, IEEE Transactions on Medical Imaging, Jun. 2002, vol. 21, No. 6, pp. 560-565.

Lebar, et al, Inter-pulse interval between rectangular voltage pulses affects electroporation threshold of artifical lipid bilayers, IEEE Transactions on Nanobioscience, Sep. 2002, vol. 1, No. 3, pp. 116-120.

Sersa, et al, Reduced blood flow and oxygenation in SA-I tumors after electrochemotherapy with cisplatin, 2003, 87, pp. 1047-1054.

Davalos, Real-time imaging for molecular medicine through electrical impedance tomography of electroporation, Dissertation, Univeristy of California, Berkeley.

Coates, et al, The electric discharge of the electric eel, *Electrophorus electricus* (Linnaeus), Zoologica: New York Zoological Society, pp. 1-32.

Lynn, et al, A new method for the generation and use of focused ultrasound in experimental biology, pp. 179-193.

Clark, et al, The Electrical Properties of Resting and Secreting Pancreas, pp. 247-260.

Neumann, Rosenheck, Permeability changes induced by electric impulses in vesicular membranes, J. Membrane Biol., 1972, 10, pp. 279-290.

Crowley, Electrical breakdown of bimolecular lipid membranes as an electromechanical instability, Biophysical Journal, 1973, vol. 13, 711-724.

Zimmermann, et al, Dielectric breakdown of cell membranes, Biophysical Journal, 1974, vol. 14, pp. 881-899.

Organ, Electrophysiologic principles of radiofrequency lesion making, Appl. Neurophysiol., 1976, 39, pp. 69-76.

Kinosita, Jr., Tsong, Hemodialysis of human erythrocytes by a transient electric field, Biochemistry, 1977, vol. 74, No. 5, pp. 1923-1927.

Kinsoita, Jr., Tsong, Formation and resealing of pores of controlled sizes in human erythrocyte membrane, Aug. 1977, vol. 268, pp. 438-441.

Kinosita, Jr., Tsong, Voltage-induced pore formation and hemolysis of human erythrocytes, Biochimica et Biophysica Acta, 1977, pp. 227-242.

Baker, Knight, Calcium-dependent exocytosis in bovine adrenal medullary cells with leaky plasma membranes, Nature, Dec. 1978, vol. 276, pp. 620-622.

Gauger, Bentrup, A study of dielectric membrane breakdown in the Fucus egg, J. Membrane Biol., 1979, 48, pp. 249-264.

Erez, Shitzer, Controlled destruction and temperature distributions in biological tissues subjected to monactive electrocoagulation, Transactions of theASME, Feb. 1980, vol. 102, pp. 42-49.

Neumann, et al, Gene transfer into mouse lyoma cells by electroporation in high electric fields, The EMBO Journal, 1982, vol. 1, No. 7, pp. 841-845.

Seibert, et al, Clonal variation of MCF-7 breast cancer cells in vitro and in athymic nude mice, Cancer Research, May 1983, 43, pp. 2223-2239.

Brown, Phototherapy of tumors, World J. Surg., 1983, 7, 700-709.

Onik, et al, Ultraonic characteristics of frozen liver, Cryobiology, 1984, 21, pp. 321-328.

Gilbert, et al, The use of ultrsound imaging for monitoring cryosurgery, IEEE Frontiers of Engineering and computing in Health Care, 1984, pp. 107-111.

Onik, et al, Sonographic monitoring of hepatic cryosurgery in an experimental animal model, AJR, May 1985, 144, pp. 1043-1047.

Griffiths, The importance of phase measurement in e lectrical impedance tomography, Phys. Med. Biol., Nov. 1987, vol. 32, No. 11, pp. 1435-1444.

Okino, Mohri, Effects of high-voltage electrical impulse and an anticancer drug on in vivo growing tumors, Jpn. J. Cancer Res., Dec. 1987, 78, pp. 1319-1321.

Kinosita, Jr. et al, Electroporation of cell membrane visualized under a pulsed-laser fluorescence microscope, Biophys. J., Jun. 1988, vol. 53, pp. 1015-1019.

Amasha, et al, Quantitative assessment of impedance tomography for temperature measurements in microwave hyperthermia, Clin. Phys. Physiol. Meas., 1988, vol. 9, Suppl. A, pp. 49-53.

Asmai, et al, Dielectric properties of mouse lymphocytes and erythrocytes, Biochimica et Biophysica Acta, 1989, 1010, pp. 49-55.

Griffiths, Zhang, A dual-frequency electrical impedance tomography system, Phys. Med. Biol., 1989, vol. 34, No. 10, pp. 1465-1476.

Rowland, et al, Transvenous ablation of atrioventricular conduction with a low energy power source, Br Heart J, 1989, 62, pp. 361-366.

Marsazalek, et al, Schwan equation and transmembrane potential induced by alternating electric field, Biophysical Journal, Oct. 1990, vol. 58, pp. 1053-1058.

Tekle, et al, Electroporation by using bipolar oscillating electric field: An improved method for DNA transfection of NIH 3T3 cells, Biochemistry, May 1991, vol. 88, pp. 4230-4234.

Mir, et al, Electrochemotherapy potentiation of antitumour effect of bleomycin by local electric pulses, Eur. J. Cancer, 1991, vol. 27, No. 1, pp. 68-72.

Mir, et al, Electrochemotherapy, a novel antitumor treatment: first clinical trial, Cancerology, 1991, 313, pp. 613-618.

Narayan, Dahiya, Establishment and characterization of a human primay prostatic adenocarcinoma cell line (ND-1_, The Journal of Urology, Nov. 1992, vol. 148, pp. 1600-1604.

Griffiths, et al, Measurement of pharyngeal transit time by electrical impedance tomography, Clin. Phys. Physiol. Meas., 1993, vol. 13, Suppl. A, pp. 197-200.

Rols, et al, Highly efficient transfection of mammalian cells by electric field pulses application to large volumes of cell culture by using a flow system, Eur. J. Biochem., 1992, 205, pp. 115-121.

Brown, et al, Blood flow imaging using electrical impedance tomography, Clin. Phys. Physiol. Meas., 1992, vol. 13, Suppl. A, pp. 175-179.

Foster, et al, Production of prostatic lesions in canines usign transrectally administered high-intensity focused ultrasound, Eur Urol, 1993, pp. 330-336.

Shiina, et al, Percutaneous ethanol injection therapy for hepatocellular carcinoma: Results in 146 patients, AJR, May 1993, 160, pp. 1023-1028.

Salford, et al, A new brain tumour therapy combining bleomycin with in vivo electropermeabilization, Biochemical and Biohysical Research Communications, Jul. 30, 1993, vol. 194, No. pp. 938-943.

(56) References Cited

OTHER PUBLICATIONS

Glidewell, Ng, The use of magnetic resonance imaging data and the inclusion of anisotropic regions in electrical impedance tomography, ISA, 1993, pp. 251-257.
Gascoyne, et al, Membrane changes accompanying the induced differentiation of Friend murine erythroleukemia cells studied by dielectrophoresis, Biochimca et Biophysica Acta, 1993, 1149, pp. 119-126.
Foster, et al, High-intensity focused ultrsound in the treatment of prostatic disease, Eur Urol, 1993, 23(suppl1), pp. 29-33.
Andreason, Electroporation as a technique for the ransfer of macromolecules into mamalian cell lines, J. Tiss. Cult. Meth., 1993, 15, pp. 56-62.
Weaver, Electroporation: A general phenomenon for manipulating cells and tissues, Journal of Cellular Biochemistry, 1993, 51, pp. 426-435.
Barber, Electrical impedance tomography applied potential tomography, Advances in Biomedical Engineering, 1993, IOS Press, pp. 165-173.
Cook, et al, ACT3: a high-speed, high-precision electrical impedance tomograph, IEEE Transactions on Biomedical Engineering, 1994, vol. 41, No. 8, pp. 713-722.
Alberts, et al, Molecular biology of the Cell, Biocchemical education, 1994, 22(3), pp. 164.
Hughes, et al, An analysis of studies comparing electrical impedance tomography with x-ray videofluoroscopy in the assessment of swallowing, Physiol. Meas. 1994, 15, pp. A199-A209.
Griffiths, Tissue spectroscopy with electrical impedance tomography: Computer simulations, IEEE Transactions on Biomedical Engineering, Sep. 1995, vol. 42, No. 9, pp. 948-954.
Gencer, et al, Electrical impedance tomography: Induced-currentimaging achieved with a multiple coil system, IEEE Transactions on Biomedical Engineering, Feb. 1996, vol. 43, No. 2, pp. 139-149.
Weaver, Chizmadzhev, Review Theory of electroporation: a review, Biolectrochemistry and Bioenergetics, 1996, 41, pp. 135-160.
Gimsa, et al, Dielectric spectroscopy of single human erythrocytes at physiological ionic strength: Dispersion of the cytoplasm, Biophysical Journal, Jul. 1996, vol. 71, pp. 495-506.
Wright, On a relationship betweene the arrhenius parameters from thermal damage studies, Technical Brief, Journal of Biomechanical Engineering, Transactions of the ASME, Apr. 2003, vol. 125, pp. 300-304.
Heczynska, et al, Hypoxia promotes a dedifferentiated phenotype in ductal breast carcinoma in situ, Cancer Research, Apr. 1, 2003, 63, pp. 1441-1444.
Ivorra, Bioimpedance monitoring for physicians: an overview, Biomedical Applications Group, Centre Nacional de Microelectronica, Jul. 2003, pp. 1-35.
Weaver, Electroporation of biological membranes from multicellular to nano scales, IEEE Transactions on Dielectrics and Electrical Insulation, Oct. 2003, vol. 10, No. 5, pp. 754-768.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Rajagopal, Rockson, Coronary restenosis: A review of mechanisms and management, The American Journal of Medicine, Nov. 2003, vol. 115, pp. 547-553.
Sersa, et al, Tumor blood flow modifying effects of electrochemotherapy: a potential vascular targeted mechanism, Radiol Oncol, 2003, 37, 1, pp. 43-48.
Davalos, et al, Theoretical analysis of the thermal effects during in vivo tissue electroporation, Bioelectrochemistry, 2003, 61, pp. 99-107.
Gothelf, et al, Electrochemotherapy: results of cancer treatment using enhanced delivery of bleomycin by electroporation, Cancer Treatment Reviews, 2003, 39, pp. 371-387.

Bancroft, et al, Design of a flow perfusion bioreactor system for bone tissue-engineering applications, Tissue Engineering, 2003, vol. 9, No. 3, pp. 549-554.
Malpica, et al, Grading ovarian serous carcinoma using a two-tier system, Am J Surg Pathol, Apr. 2004, vol. 28, No. 4, pp. 496-504.
Davalos, et al, Electrical impedance tomography for imaging tissue electroporation, IEEE Transactions on Biomedical Engineering, May 2004, vol. 51, No. 5, pp. 761-767.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Radeva, et al, Induction of apoptosis and necrosis in cancer cells by electric fields, electromagnetic fields, and photodynamically active quinoids, Electromagnetic Biology and Medicine, 2003, 23, pp. 185-200.
Davalos, et al, Tissue ablation with irreversible electroporation, Annals of Biomedical Engineering, Feb. 2005, vol. 33, No. 2, pp. 223-231.
Sel, et al, Sequential finite element model of tissue electropermeabilization, IEEE Transactions on Biomedical Engineering, May 2005, vol. 52, No. 5, pp. 816-827.
Dean, Nonviral gene transfer to skeletal, smooth, and cardiac muscle in living animals, Am J Physiol cell Physiol, Aug. 2005, 289, pp. C233-C245.
Pavselj, et al, The course of tissue permeabilization studied on a mathematical model of a subcutaenous tumor in small animals, IEEE Transactions on Biomedical Engineering, Aug. 2005, vol. 52, No. 8, pp. 1373-1381.
Paszek, et al, Tensional homeostasis and the malignant phenotype, Cancer Cell, Sep. 2005, vol. 8, pp. 241-254.
Saur, et al, CXCR4 expression increases liver and lung metastasis in a mouse model of pancreatic cancer, Basic-Liver, pancreas, and biliary tract, Gastroenterology, Oct. 2004, 129, pp. 1237-1250.
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Miller, et al, Cancer cells ablation with irreversible electroporation, Technology in Cancer Research and Treatment, Dec. 2005, vol. 4, No. 6, pp. 699-705.
Mir, et al, Electric pulse-mediated gene delviery to various animal tissues, Advances in Genetics, 2005, vol. 54, pp. 84-114.
Nikolski, Efimov, Electroporation of the heart, Europace, 2005, 7, pp. S146-S154.
Machado-Aranda, et al, Gene transfer of the Na+, K+K-ATPase B1 subunit using electroporation increases lung liquid clearance, American Journal of Respiratory and Critical Care Medicine, 2004, vol. 171, pp. 204-211.
Kotnik, Miklavcic, Theoretical evaluation of voltage inducement on internal membranes of biological cells exposed to electric fields, Biophysical Journal, Jan. 2006, vol. 90, pp. 480-491.
Labeed, et al, Differences in the biophysical properties of membrane and cytoplasm of apoptotic cells revealed using dielectrophoresis, Biochimica et Biophysica Acta, Feb. 23, 2006, 1760, pp. 922-929.
Pucihar, et al, Numerical determination of transmembrane voltage indcued on irregularly shaped cells, Annals of Biomedical Engineering, Mar. 18, 2006, vol. 34, No. 4, pp. 642-652.
Gilbert, et al, Decellularization of tissues and organs, Biomaterials, Mar. 7, 2006, 27, pp. 3675-3683.
Edd, et al, In vivo results of a new focal tissue ablation technique: Irreversible electroporation, IEEE Transactions on Biomedical Engineering, Jun. 2006, vol. 53, No. 5, pp. 1409-1415.
Ivorra, Rubinsky, Impedance analyzer for in vivo electroporation studies, Proceedings of the 28th IEEE EMBS Annual International Conference, IEEE, Aug. 30, 2006, pp. 5056-5059.
Carpenter, et al, CellProfiler: image analysis software for identifying and quantifying cell phenotypes, Genome Biology, Oct. 31, 2006, vol. 7, Iss. 10, R100, pp. 1-11.

(56) References Cited

OTHER PUBLICATIONS

Kanduser, et al, Cell membrane fluidity related to electroporation and resealing, Eur Biophys J, Oct. 8, 2006, 35, pp. 196-204.
Bolland, et al, Development and characterisation of a full-thickness acellular porcine bladder matrix for tissue engineering, Biomaterials, Nov. 7, 2006, 28, pp. 1061-1070.
Cukjati, et al, Real time electroporation control for accurate and safe in vivo non-viral gene therapy, Bioelectrochemistry, Nov. 10, 2006, 70, pp. 501-507.
Tijink, et al, How we do it: Chemo-electroporation in the head and neck for otherwise untreatable patients, Correspondence, Clinical Otolaryngology, 2006, 31, pp. 447-451.
Marty, et al, Electrochemotherapy—An easy, highly effective and safe treatment of cutaneous and subcutaneous metastases: Results of ESOPE (European Standard Operating Procedures of Electrochemotherapy) study, EJC Supplements, 2006, 4, pp. 3-13.
Soden, et al, Successful application of targeted electrochemotherapy using novel flexible electrodes and low dose bleomycin to solid tumors, Cancer Letters, 2006, 232 pp. 300-310.
Demirbas, Thermal energy storage and phase change materials: An overview, Energy Sources, Part B, 2006, 1, pp. 85-95.
Rubinsky, et al, Irreversible electroporation: A new ablation modality—Clinical implications, Technology in Cancer Research and Treatment, Feb. 2007, vol. 6, No. 1, pp. 1-12.
Zhou, et al, Electroporation-mediated transfer of plasmids to the lung results in reduced TLR9 signaling and inflammation, Gene Therapy, Mar. 8, 2007, 14, pp. 775-780.
Lavee, et al, A novel nonthermal energy source for surgical epicardial atrial ablation: Irreversible electroporation, The Heart Forum, Mar. 2007, 10, 2, pp. 96-101.
Hall, et al, Nanosecond pulsed electric fields induce apoptosis in p53-wildtype and p53-null HCT116 colon carcinoma cells, Apoptosis, May 23, 2007, 12, pp. 1721-1731.
Sel, et al, Feasibility of employing model-based optimization of pulse amplitude and electrode distance for effective tumor electropereabilization, IEEE Transactions on Biomedical Engineering, May 2007, vol. 54, No. 5, pp. 773-781.
Kirson, et al, Alternating electric fields arrest cell proliferation in animal tumor models and human brain tumor, PNAS, Jun. 12, 2007, vol. 104, No. 24, pp. 10152-10157.
Talele, Gaynor, Non-linear time domain model of electropermeabilizationi: Response of a single cell to an arbitary applied electric field, Journal of Electrostatics, Jul. 16, 2007, 65, pp. 775-784.
Esser, et al, Towards solid tumor treatment by irreversible electroporation: Intrinsic redistribution of fields and currents in tissue, Technology in Cancer Research and Treatment, Aug. 2007, vol. 6, No. 4, pp. 261-273.
Maor, et al, The effect of irreversible electroporation on blood vessels, Technology in Cancer Research and Treatment, Aug. 2007, vol. 6, No. 4, pp. 307-312.
Edd, Davalos, Mathematical modeling of irreversible electroporation for treatment planning, Technology in Cancer Research and Treatment, Aug. 2007, vol. 6, No. 4, pp. 275-286.
Rubinsky, Irreversible electroporation in medicine, Technology in Cancer Research and Treatment, Aug. 2007, vol. 6, No. 4, pp. 255-259.
Onik, et al, Irreversible electroporation: Implications for prostate ablation, Technology in Cancer Research and Treatment, Aug. 2007, vol. 6, No. 4, pp. 295-300.
Lee, et al, Imaging guided percutaneous irreversible electroporation: Ultrasound and immunohistological correlation, Technology in Cancer Research and Treatment, Aug. 2007, vol. 6, No. 4, pp. 287-293.
Bertacchini, et al, Design of an irreversible electroporation system for clinical use, Technology in Cancer Research and Treatment, Aug. 2007, vol. 6, No. 4, pp. 313-320.
Al-Sakere, et al, A study of the immunological response to tumor ablation with irreversible electroporation, Technology in Cancer Research and Treatment, Aug. 2007, vol. 6, No. 4, pp. 301-305.

Fischbach, et al, Engineering tumors with 3D scaffolds, Nature Methods, Sep. 2, 2007, vol. 4, No. 10, pp. 855-860.
Ivorra, Rubinsky, In vivo electrical impedance measurements during and after electroporation of rat liver, Bioelectrochemistry, Oct. 21, 2007, 70, pp. 287-295.
Yao, et al, Study of transmembrane potentials of inner and outer membranes induced by pulsed-electric-field model and simulation, IEEE Transactions on Plasma Science, Oct. 2007, vol. 35, No. 5, pp. 1541-1549.
Corovic, et al, Analytical and numerical quantification and comparison of the local electric field in the tissue for different electrode configurations, BioMedical Engineering Online, Oct. 15, 2007, 6, 37, pp. 1-14.
Schoenbach, et al, Bioelectric effects of intense nanosecond pulses, IEEE Transactions on Dielectric and Electrical Insulation, 2007, vol. 14, Iss. 5, pp. 1088-1109.
Al-Sakere, et al, Tumor ablation with irreversible electroporation, PLOS One, Nov 7, 2007, Iss. 11, e1135, pp. 1-8.
Hall, et al, Nanosecond pulsed electric fields have differential effects on cells in the S-phase, DNA and Cell Biology, 2007, vol. 26, No. 3, pp. 160-171.
He, et al, Nonlinear current response of micro electroporation and resealing dynamics for human cancer cells, Bioelectrochemistry, Jan. 29, 2008, 72, pp. 161-168.
Ott, et al, Perfusion-decellarized matrix: using nature's platform to engineer a bioartificial heart, Nature Medicine, Jan. 13, 2008, vol. 14, No. 2, pp. 213-221.
Ron, et al, Cell-based screening for membranal and cytoplasmatic markers using dielectric spectroscopy, Biophysical Chemistry, Mar. 29, 2008, 135, pp. 59-68.
Garcia, et al, Irreversible electroporation (IRE) to treat brain tumors, Proceedings of the ASME 2008 Summer Bioengineering Conference (SBC2008), Jun. 25, 2008, pp. 6-7.
Davalos, Rubinsky, Temperature considerations during irreversible electroporation, International Journal of Heat and Mass Transfer, Jun. 14, 2008, 51, pp. 5617-5622.
Dahl, et al, Nuclear shape, mechanics and mechanotransduction, Circulation Research, Jun. 6, 2008, 102, pp. 1307-1318.
Seidler, et al, A Cre-IoxP-based mouse model for conditional somatic gene expression and knockdown in vivo by using avian retroviral vectors, PNAS, Jul. 22, 2008, vol. 105, No. 29, pp. 10137-10142.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Jensen, et al, Tumor volume in subcutaneous mouse xenografts measured by microCT is more accurate and reproducible than determined by 18F-FDG-microPET or external caliper, BMC Medical Imaging, Oct. 16, 2008, 8, 16,m pp. 1-9.
Rubinsky, et al, Optimal parameters for the destruction of prostate cancer using irreversible electroporation, The Journal of Urology, Dec. 2008, vol. 180, pp. 2668-2674.
Daud, et al, Phase I trial of Interleukin-12 plasmid electroporation in patients with metastatic melanoma, Journal of Clinical Oncology, Dec. 20, 2008, vol. 26, No. 36, pp. 5896-5903.
Flanagan, et al, Unique dielectric properties distinguish stem cells and their differentiated progency, Stem Cells, 2008, 26, pp. 656-665.
Mali, et al, The effect of electroporation pulses on functioning of the heart, Med Biol Eng Comput, 2008.
Kuthi, Gundersen, Nanosecond uplse generator with scalable pulse amplitude, IEEE, 2008, pp. 65-68.
Craiu, Scadden, Chapter 22 flow electroporation with pulsed electric fields for purging tumor cells, Electroporation Protocols: Preclinical and Clinical Gene Medicine, Methods in Molecular Biology, vol. 423, pp. 301-310.
Mir, Chapter 1 application of electroporation gene therapy: Past, current and future, Electroporation Protocols: Preclinical and Clinical Gene Medicine, Methods in Molecular Biology, vol. 423, pp. 3-17.

(56) References Cited

OTHER PUBLICATIONS

Lin, Lee, An optically induced cell lysis device using dielectrophoresis, Applied Physics Letters, Jan. 20, 2009, 94, 033901, pp. 1-3.

Kroeger, et al, Curvature-driven pore growth in charged membranes during charge-pulse and voltage-clamp experiments, Biophysical Journal, Feb. 2009, 96, 3, pp. 907-916.

Maor, et al, Non thermal irreversible electroporation: Novel technology for vascular smooth muscle cells abation, PLOS One, Mar. 9, 2009, vol. 4757-, Iss. 3, e4757, pp. 1-9.

Shafiee, et al, A preliminary study to delineate irreversible electroporation from thermal damage using the Arrhenius equation, Journal of Biomedical Engineering, Jul. 2009, vol. 131, 074509, pp. 1-5.

Granot, et al, In vivo imaging of irreversible electroporation by means of electrical impedance tomography, Phys. Med. Biol., Jul. 30, 2009, 54, pp. 4927-4943.

Daniels, Rubinsky, Electrical field and temperature model of nonthermal irreversible electroporation in heterogeneous tissues, Journal of Biomedical Engineering, Jul. 2009, vol. 131, 071006, pp. 1-12.

Esser, et al, Towards solid tumor treatment by nanosecond pulsed electric fields, Technology in Cancer Research and Treatment, Aug. 2009, vol. 8, No. 4, pp. 289-306.

Ivorra, et al, In vivo electrical conductivity measurements during and after tumor electroporation: conductivity changes reflect the treatment,Phys. Med. Biol., Sep. 17, 2009, 54, pp. 5949-5963.

Garcia, et al, Pilot study of irreversible electroporation for intracranial surgery, 31st Annual International Conference of the IEEE EMBS, IEEE, Sep. 2, 2009, pp. 6513-6516.

Hong, et al, Cardiac ablation via electroporation, 31st Annual International Conference of the IEEE EMBS, IEEE, Sep. 2, 2009, pp. 3381-3384.

Neal, Davalos, The feasibility of irreversible electroporation for the treatment of breast cancer and other heterogeneous systems, Annals of Biomedical Engineering, Dec. 2009, vol. 37, No. 12, pp. 2615-2625.

Sharma, et al, Review on thermal energy storage with phase change materials and applications, Renewable and Sustainable Energy Reviews, 2009, 13, pp. 318-345.

Ibey, et al, Selective cytotoxicity of intense nanosecond-duration electric pulses in mammalian cells, Biochim Biophys Acta, Nov. 2010, 1800, 11, pp. 1210-1219.

Tsivian, Polascik, Recent advances in focal therapy of prostate and kidney cancer, Medicine Reports, Jan. 18, 2010, 2, 1, pp. 1-3.

adEyanju, et al, The improvement of irreversible electroporation therapy using saline-irrigated electrodes: A theoretical study, Technology in Cancer Research and Treatment, Aug. 2011, vol. 10, No. 4, pp. 347-360.

Maor, Rubinsky, Endovascular nonthermal irreversible electroporation: A finite element analysis, Journal of Biomedical Engineering, Feb. 7, 2010, vol. 132, 031008, pp. 1-7.

Choi, et al, Preclinical analysis of irreversible electroporation on rat liver tissues using a microfabricated electroporator, Tissue Engineering Part C, 2010, vol. 16, No. 6, pp. 1245-1253.

Verbridge, et al, Oxygen-controlled three-dimensional cultures to analyze tumor angiogenesis, Tissue Engineering, Part A, Apr. 9, 2010, vol. 16, No. 7, pp. 2133-2141.

Lee, et al, Advanced hepatic ablation technique for creating complete cell death: Irreversible electroporation, 2010, Radiology, vol. 255, No. 2, pp. 426-433.

Ball, et al, Irreversible electroporation: A new challenge in "out of the operating theater" anesthesia, Anesth Analg, May 2010, 110, pp. 1305-1309.

Laufer, et al, Electrical impedance characterization of normal and cancerous human hepatic tissue, Physiol Meas, 2010, 31, pp. 995-1009.

Sabuncu, et al, Dielectrophoretic separation of mouse melanoma clones, Biomicrofluidics, Jun. 16, 2010, 4, 021101, pp. 1-7.

Garcia, et al, Intracranial nonthermal irreversible electroporation: In vivo analysis, J Membrane Biol, Jul. 29, 2010, 236, pp. 127-136.

Neal, et al, Treatment of breast cancer through the application of irreversible electroporation using a novel minimally invasive single needle electrode, Breat Cancer Res Treat, Aug. 27, 2010, 123, 1, pp. 295-301.

Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-432.

Neal, et al, A study using irreversible electroporation to treat large, irregular tumors in a canine patient, 32nd Annual International Conference of the IEEE EMBS, IEEE, Aug. 2010, pp. 2747-2750.

Garcia, et al, Non-thermal irreversible electroporation for deep intracranial disorders, 32nd Annual International Conferenece of the IEEE EMBS, IEEE, Aug. 2010, pp. 2747463.

Phillips, et al, Nonthermal irreversible electroporation for tissue decellularization, Journal of Biomedical Engineering, Aug. 16, 2010, vol. 132, 091003, pp. 1-8.

Pech, et al, Irreversible electroporation of renal cell carcinoma: A first-in-man phase I clinical study, Cardiovasc Intervent Radiol, Aug. 15, 2010.

Lee, et al, Irreversible electroporation: A novel image-guided cancer therapy, Gut and Liver, Sep. 2010, vol. 4, Supp. 1, pp. S99-104.

Hong, et al, Cardiac ablation via electroporation, 31st Annual International Conference of the IEEE EMBS, IEEE, Sep. 2, 2010, pp. 3381-3384.

Dupuy, et al, Irreversible electroporation in a swine lung model, Cardiovasc Intervent Radiol, Dec. 30, 2010, 34, pp. 391-395.

Arena, et al, Theoretical considerations of tissue electropration with high frequency biopolar pulses, IEEEE, pp. 1-7.

Deodhar, et al, Renal tissue ablation with irreversible electroporation: Preliminary results in a porcine model, Technology and Engineering, Urology, 2010, 1-7.

McCarley, Soulen, Percutaneous ablation of hepatic tumors, Seminars in Interventional Radiology, 2010, vol. 27, No. 3, pp. 255-260.

Neu, Neu, Mechanism of irreversible electroporation in cells: Insight from the models, Irreversible Electroporation: Biomed, pp. 85-122.

Charpentier, et al, Irreversible electroporation of the pancreas in swine: A pilot study, HPB, 2010, 12, pp. 348-351.

Tracy, et al, Irreversible electroporation (IRE): A novel method for renal tissue ablation, BJU International, 107, pp. 1982-1987.

Onik, Rubinsky, Irreversible electroporation: First patient experience focal therapy of prostate cancer, Irreversible Electroporation, Biomed, pp. 235-247.

McWilliams, et al, Image-guided tumor ablation: Emerging technologies and future directions, Seminars in Interventional Radiology, 2010, vol. 27, No. 3, pp. 302-313.

Kurup, Callstrom, Image-guided percutaneous ablation of bone and soft tissue tumors, Seminars in Interventional Radiology, 2010, vol. 27, No. 3, pp. 276-284.

Thomson, Human experience with irreversible electroporation, Irreversible Electroporation, Biomed, 2010, pp. 249-354.

Saldanha, et al, Current tumor ablation technologies: Basic science and device review, Seminars in Interventional Radiology, 2010, vol. 27, No. 3, pp. 247-254.

Dupuy, Shulman, Current status of thermal ablation treatments for lung malignancies, Seminars in Interventional Radiology, 2010, vol. 27, No. 3, pp. 268-275.

Carmi, Georgiades, Combination percutaneous and intraarterial therapy for the treatment of hepatocellular carcinoma: A review, Seminars in Interventional Radiology, 2010, vol. 27, No. 3, pp. 296-301.

Jarm, et al, Antivascular effects of electrochemotherapy: implicatoins in treatment of bleeding metastases, Expert Rev. Anticancer Ther., 2010, 10, 5, pp. 729-746.

Maybody, An overview of image-guided percutaneous ablation of renal tumors, Seminars in Interventional Radiology, 2010, vol. 27, No. 3, pp. 261-267.

Goldberg, Rubinsky, A statistical model for multidimensional irreversible electroporation cell death in tissue, Biomedical Engineering Online, 2010, 9:13, pp. 1-13.

(56) References Cited

OTHER PUBLICATIONS

Sano, et al, Towards the creation of decellularized organ constructs using irreversible electroporation and active mechanical perfusion, Biomedical Engineering Online, 2010, 9, 83, pp. 1-16.

Mahmood, Gehl, Optimizing clinical performance and geometrical robustness of a new electrode device for intracranial tumor electroporation, Bioelectrochemistry, Jan. 6, 2011, 81, pp. 10-16.

Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.

Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.

Bower, et al, Irreversible electroporation of the pancreas: Definitive local therapy without systemic effects, Journal of Surgical Oncology, Feb. 28, 2011, 104, pp. 22-28.

Ellis, et al, Nonthermal irreversible electroporation for intracranial surgical applications, J Neurosurg, Mar. 2011, 114, pp. 681-688.

Nesin, et al, Manipulation of cell volume and membrane pore comparision following single cell permeabilization with 60- and 600-ns electric pulses, Biochim Biophys Acta, Mar. 2011, 1808(3), pp. 792-801.

McCall, Nanoknife, liposomal doxorubicin show efficacy against liver cancer, European Congress of Radiology, Mar. 7, 2011, pp. 1-2.

Mahmood, et al, Diffusion-weighted MRI for verification of electroporation-based treatments, J Membrane Biol, Mar. 6, 2011, 240, pp. 131-138.

Deodhar, et al, Irreversible electroporation near the heart: Ventricular arrhythmias can be prevented with ECG synchronization, AJR, Mar. 2011, 196, pp. W330-W335.

Garcia, et al, A parametric study delineating irreversible electroporation from thermal damage based on a minimally invasive intracranial procedure, Biomedical Engineering Online, 2011, 10: 34, pp. 1-21.

Li, et al, The effects of irreversible electroporation (IRE) on nerves, PLOS One, Apr. 14, 2011, vol. 6, Iss. 4, e18831, pp. 1-7.

Neal, et al, Successful treatment of a large soft tissue sarcoma with irreversible electroporaiton, Journal of Clinical Oncology, May 1, 2011, vol. 29, No. 13, pp. e372-e377.

Thomson, et al, Investigation of the safety of irreversible electroporation in humans, J Vasc Interv Radiol, May 2011, 22, pp. 611-621.

Rossmeisl, Jr., et al, Successful treatment of a large soft tissue sarcoma with irreversible electroporation, Journal of Clinical Oncology, May 1, 2011, vol. 29, No. 13, pp. e372-e377.

Daniels, Rubinsky, Temperature modulation of electric fields in biological matter, PLOS One, vol. 6, Iss. 6, e20877, pp. 1-9.

Lion, et al, Poly(I:C) enhances the susceptibility of leukemic cells to NK cell cytotoxicity and phagocytosis by DC, PLOS One, vol. 6, Iss. 6, e20952, pp. 1-10.

Agerholm-Larsen, et al, Preclinical validation of electrochemotherapy as an effective treatment for brain tumors, Cancer Res, Jun. 1, 2011, 71, 11, pp. 3753-3762.

Mulhall, et al, Cancer, pre-cancer and normal oral cells distinguished by dielectrophoresis, Anal Bioanal chem, Aug. 30, 2011, 401, pp. 2455-2463.

Troszak, Rubinsky, Self-powered electroporation using a singularity-induced nano-electroporation configuration, Biochemical and Biophysical Research Communications, Sep. 28, 2011, 414, pp. 419-424.

Arena, et al, High-frequency irreversible electroporation (H-FIRE) for non-thermal ablation without muscle contraction, BioMedical Engineering Online, Nov. 21, 2011, 10: 102, pp. 1-20.

Hjouj, et al, Electroporationo-induced BBB disruption and tissue damage depicted by MRI, Neuro-Oncology, Abstracts from the 16th Annual Scientific Meeting, Nov. 17, 2011, vol. 13, Supp 3, ET-32, p. iii114.

Mir, Orlowski, Introduction: Electropermeabilization as a new drug delivery approach, Methods in Molecular Medicine, 2000, vol. 37, pp. 99-117.

O'Brien, et al, Investigation of the Alamar Blue (resarzurin) fluorescent dye for the assessment of mammalian cell cytotoxicity, Eur J Biochem, 2000, 267, pp. 5421-5426.

Szot, et al, 3D in vitro bioengineered tumors based on collagen I hydrogels, Biomaterials, Nov. 2011, 32(31), pp. 7905-7912.

Bastista, et al, The use of whole organ decellularization for the generation of a vascularized liver organoid, Hepatology, 2011, vol. 53, No. 2, pp. 604-617.

Sano, et al, Modeling and development fo a low frequency contactless dielectrophoresis (cDEP) platform to sort cancer cells from dilute whole blood samples, Biosensors and Bioelectronics, 2011, pp. 1-8.

Charpentier, et al, Irreversible electroporation of the liver an dliver hilum in swine, HBP, 2011, 13, pp. 168-173.

Sankaranarayanan, et al, Effect of irreversible electroporation on cell proliferation in fibroblasts, Proc. ESA Annual Meeting on Electrostatics, 2011, pp. 1-8.

Sano, et al, Contactless dielectrophoretic spectroscopy: Examination of the dielectric properties of cells found in blood, Electrophoresis, 2011, 32, pp. 3164-3171.

Chen, et al, Classification of cell types using a microfluidic device for mechanical and electrical measurements on single cells, Lab Chip, 2011, 11 , pp. 3174-3181.

Rebersek, Miklavcic, Advantages and disadvantages of different concepts of electroporation pulse generation, Automatika, 2011, 52, 1, pp. 12-19.

Ben-David, et al, Characterization of irreversible electroporaiton ablation in in vivo porcine liver, AJR, Jan. 2012, 198, pp. W62-W68.

Appelbaum, et al, US findings after irreversible electroporation ablation: Radiologic-pathologic correlation, Radiology, Jan. 2012, vol. 262, No. 1, pp. 117-125.

Salmanzadeh, et al, Dielectrophoretic differentiation of mouse ovarian surface epithelial cells, macrophages, and fibroblasts using contactless dielectrophoresis, Biomicrofluidics, Apr. 3, 2012, 6, 024104, pp. 1-13.

Neal, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.

Du Pre, et al, Minimal coronary artery damage by myocardial electroporation ablation, European Society of Cardiology, Europace, May 31, 2012, pp. 1-6.

Wittkampf, et al, Myocradial lesion depth with circular electroporation ablation, Circ Arrhythm Electrophysiol, 2012, 5, pp. 581-586.

Arena, et al, Phase change electrodes for reducing joule heating during irreversible electroporation, Proceedings of the ASME 2012 Summer Bioengineering Conference, Jun. 20, 2012, pp. 1-2.

Garcia, et al, Towards a predictive model of electroporation-based therapies using pre-pulse electrical measurements, 34th Annual International Conference of the IEEE EMBS, Aug. 28, 2012, pp. 2575-2578.

Hjouj, et al, MRI study on reversible and irreversible electroporation induced blood brain barrier disruption, Aug. 10, 2012, PLOS One, vol. 7, 8, e42817, pp. 1-9.

Martin, et al, Irreversible electroporation therapy in the management of locally advanced pancreatic adenocarcinoma, American College of Surgeons, Sep. 2012, vol. 215, No. 3, pp. 361-369.

Weaver, et al, A brief overview of electroporation pulse strength-duration space: A region where additional intracellular effects are expected, Bioelectrochemistry, Oct. 2012, 87, pp. 236-243.

Arena, et al, A three-dimensional in vitro tumor platform for modeling therapeutic irreversible electroporation, Biophysical Journal, Nov. 2012, vol. 103, pp. 2033-2042.

Garcia, et al, 7.0-T magnetic resonance imaging characterization of acute blood-brain-barrier disruption achieved with intracranial irreversible electroporation, PLOS One, vol. 7, 11, pp. 1-8.

(56) References Cited

OTHER PUBLICATIONS

Arena, et al, Towards the development of latent heat storage electrodes for electroporation-based therapies, Applied Physics Letters, 2012, 101, 083902, pp. 1-4.
Cannon, et al, Safety and early efficacy of irreversible electroporation for hepatic tumors in proximity to vital structures, Journal of Surgical Oncology, 2012, pp. 1-6.
Bagla, Papadouris, Percutaneous irreversible electroporation of surgically unresectable pancreatic cancer: A case report, J Vasc Interv Radiol, 2012, 23, pp. 142-145.
Phillips, et al, Irreversible electroporation on the small intestine, British Journal of Cancer, 2012, pp. 1-6.
Mahnic-Kalamiza, et al, Educational application for visualization and analysis of electric field strength in multiple electrode electroporation, BMC Medical Education, 2012, 12, 102, pp. 1-13.
Kingham, et al, Ablation of perivascular hepatic malignant tumors with irreversible electroporation, J Am Coll Surg, 2012, 215, pp. 379-387.
Salmanzadeh, et al, Investigating dielectric properties of different stages of syngeneic murine ovarian cancer cells, Biomicrofluidics, Jan. 23, 2013, 7, 011809, pp. 1-12.
Faroja, et al, Irreversible electroporation ablation: Is all the damage non-thermal?, Radiology, Feb. 2013, vol. 266, No. 2, pp. 462-470.
Fong, et al, Modeling ewing sarcoma tumors in vitro with 3D scaffolds, PNAS, Apr. 16, 2013, vol. 110, No. 15, pp. 6500-6505.
Garcia, et al, Position paper concerning the use of Angiodynamics' nanoknife system for treatment of brain gliomas, Virgina Tech—Wake Forest University, May 22, 2013, pp. 1-46.
Salmanzadeh, et al, Sphingolipid metabolites modulate dielectric characteristics of cells in a mouse ovarian cancer progression model, Integr Biol, Jun. 2013, 5, 6, pp. 843-852.
Polak, et al, On the electroporation thresholds of lipid bilayers: Molecular dynamics simulation investigations, J Membrane Biol, Jun. 13, 2013, 246, pp. 843-850.
Jiang, et al, Membrane-targeting approaches for enhanced cancer cell destruction with irreversible electroporation, Annuals of Biomedical Engineering, Aug. 15, 2013.
Bayazitoglu, et al, An overview of nanoparticle assisted laser therapy, International Journal of Heat and Mass Transfer, Sep. 11, 2013, 67, pp. 469-486.

Rossmeisl, Jr., et al, Pathology of non-thermal irreversible electroporation (N-TIRE)-induced ablation of the canine brain, Journal of Veterinary Science, 2013, 14, 4, pp. 433-440.
Lu, et al, Irreversible electroporation: Ready for prime time?, Techniques in Vascular and Interventional Radiology, 2013, 16, pp. 277-286.
Dunki-Jacobs, et al, Evaluation of resistance as a measure of successful tumor ablation during irreversible electroporation of the pancreas, American College of Surgeons, Feb. 2014, vol. 218, No. 2, pp. 179-187.
Son, et al, Basic features of a cell electroporation model: illustrative behavior for tw overy different pulses, J Membrane Biol, Jul. 22, 2014, 247, pp. 1209-1228.
Neal, et al, An "Off-the-Shelf" system for intraprocedural electrical current evaluation and monitoring of irreversible electroporation therapy, Cardiovasc Intervent Radiol, Feb. 27, 2014.
Sano, et al, In-vtro bipolar nano- and microsecond electro-pulse bursts for irreversible electroporation therapies, Bioelectrochemistry, Aug. 4, 2014, 100, pp. 69-79.
Rossmeisl, New treatment modalities for brain tumors in dogs and cats, Vet Clin Small Anim, 2014, 44, pp. 1013-1038.
Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.
Trimmer, et al, Minimally invasive percutaneous treatment of small renal tumors with irreversible electroporation: a single-center experience, J Vasc Interv Radiol, 2015, 26: pp. 1465-1471.
Eppich, et al, Pulsed electric fields for seletion of hematopoietic cells and depletion of tumor cell contaminants, Nature America, Aug. 2000, vol. 18, pp. 882-887.
Mir, Therapeutic perspectives of in vivo cell electropermeabilization, Bioelectrochemistry, 2000, 53, pp. 1-10.
Al-Khadra, et al, The role of electroporation in defibrillation, Circulation Research, Oct. 27, 2000, 87, pp. 797-804.
Miklavcic, et al, A validated model of in vivo electric field distribution in tissues for electrochemotherapy and for DNA electrotransfer for gene therapy, Biochimica et Biophysica Acta, 2000, 1523, pp. 73-83.
Rubinsky, Cryosurgery, Annu. Rev. Biomed. Eng. 2000, 2, pp. 157-187.
Jaroszeski, et al, In vivo gene delivery by electroporation, Advanced Drug Delivery Reviews, 1999, 35, pp. 131-137.

\* cited by examiner

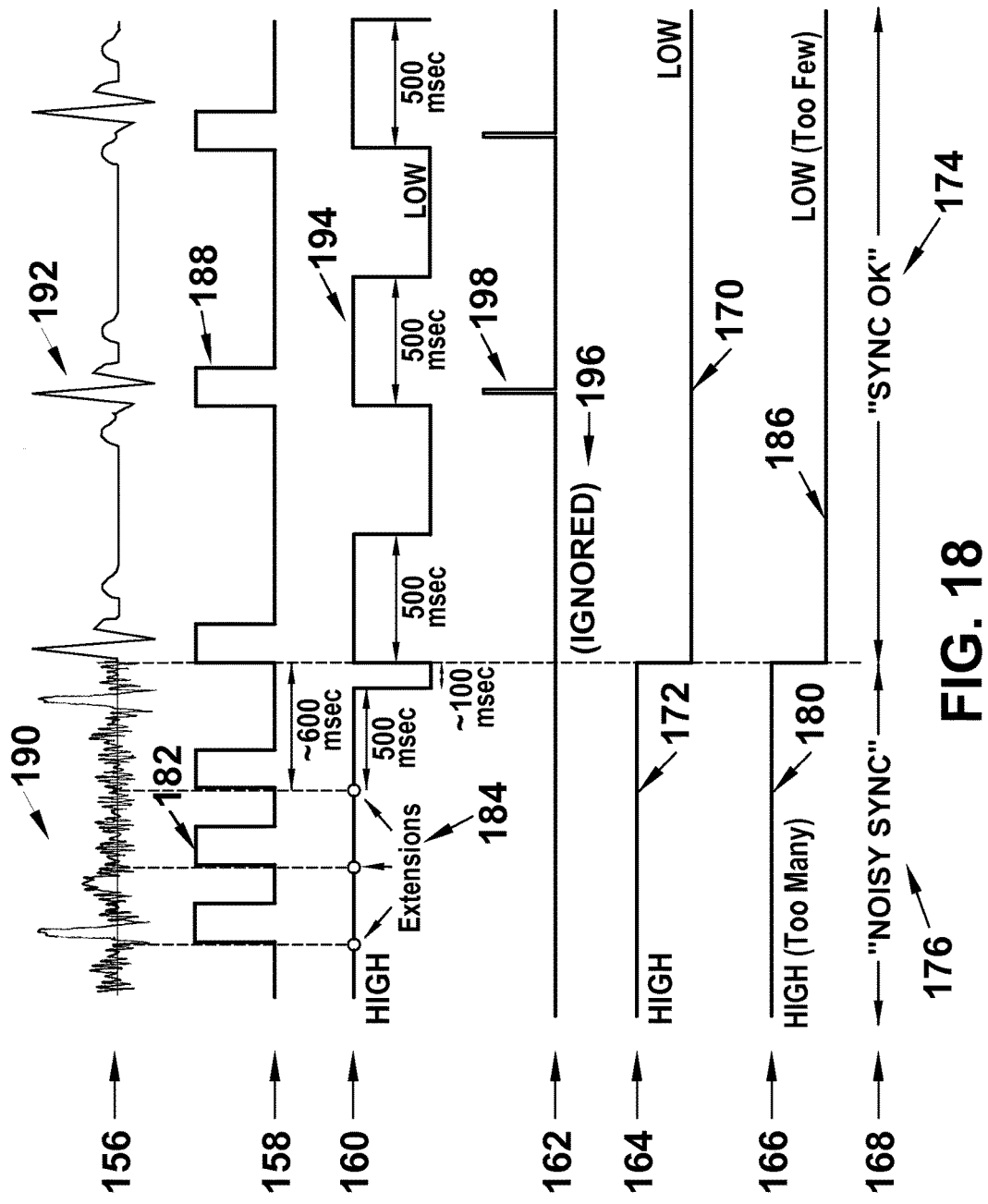

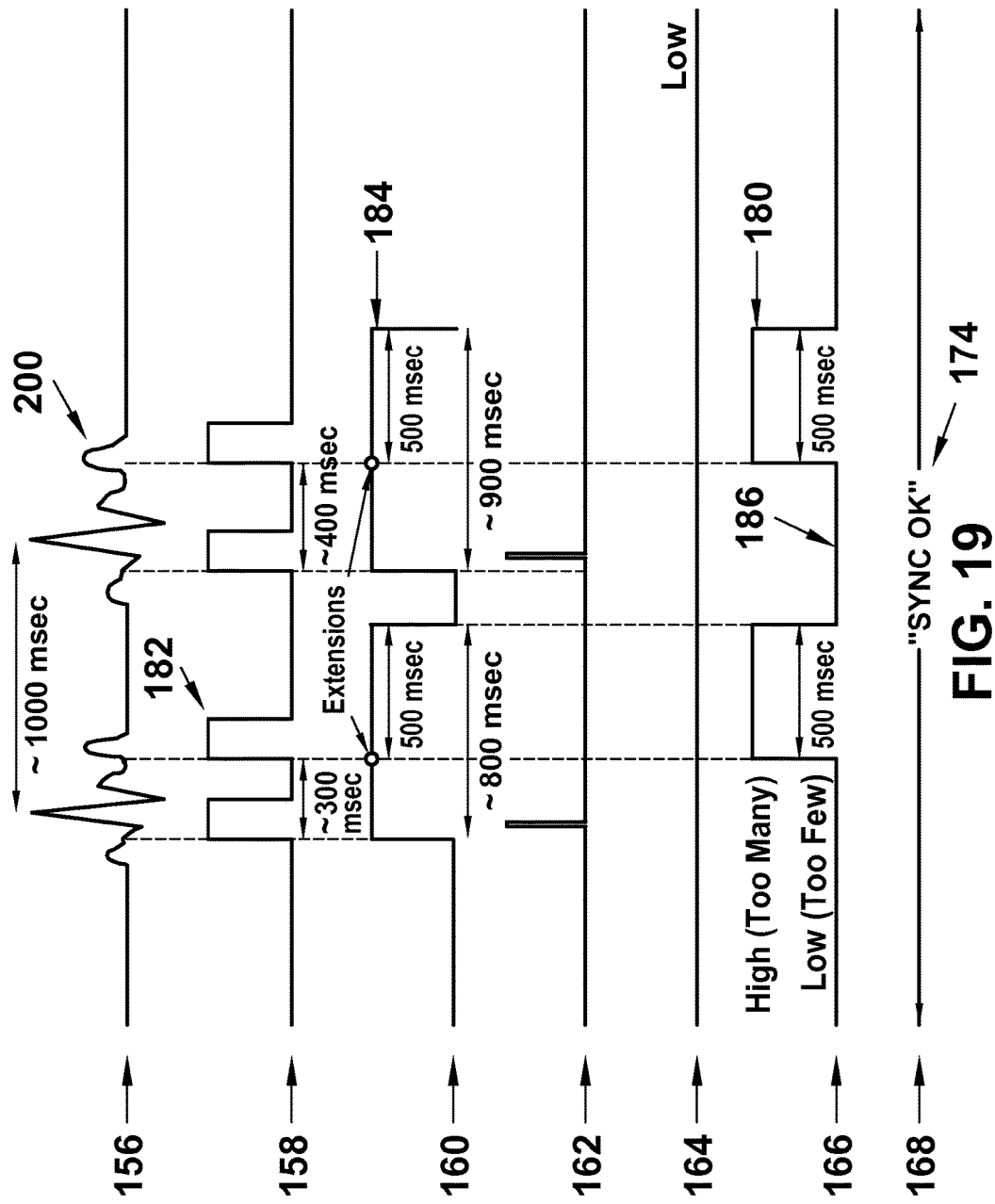

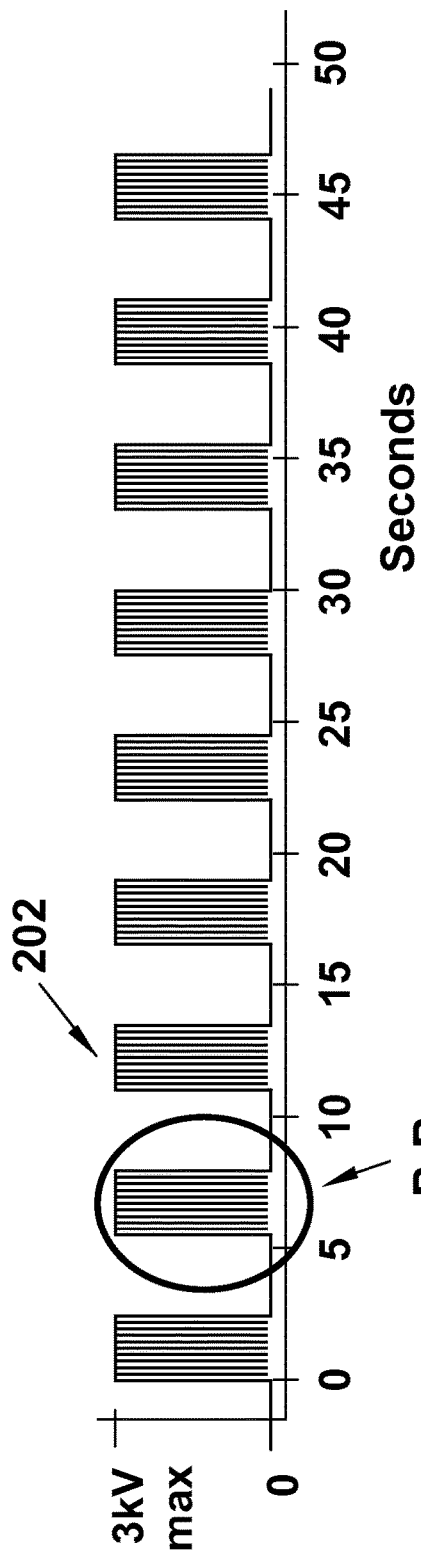
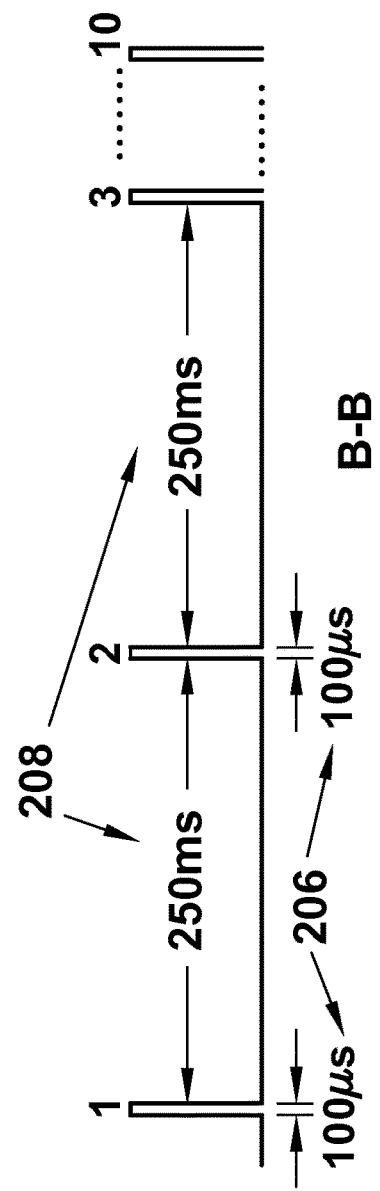
FIG. 21A
FIG. 21B

SYSTEM AND METHOD FOR SYNCHRONIZING ENERGY DELIVERY TO THE CARDIAC RHYTHM

CROSS REFERENCE TO RELATED APPLICATION

This application is a continuation of application Ser. No. 12/790,681, filed May 28, 2010, now U.S. Pat. No. 8,903,488, which claims priority under 35 U.S.C. 119(e) to U.S. Provisional Application No. 61/181,727, filed May 28, 2009, which is incorporated herein by reference.

FIELD OF THE INVENTION

The present invention relates generally to a medical treatment device. More specifically, this present invention is related to system and method for synchronizing treatment signals with a cardiac cycle.

DESCRIPTION OF THE RELATED ART

Medical devices such as those for applying reversible electroporation (RE) or irreversible electroporation (IRE) pulses are used for patient treatments, therapies, and tissue ablation with great success. As these devices generate very high voltage treatment signals of up to several thousand volts, there is a possibility that it may interfere with normal heart functions if the treatment signals are applied at the wrong time. Possible interferences may include inducing atrial and ventricular flutter and fibrillation and premature heartbeats.

To avoid such interferences, these medical treatment devices are starting to be used with synchronization devices that apply treatment pulse signals at one or more predetermined phases of the cardiac cycle such as during the refractory period of the cardiac cycle which is the period after the ventricular contraction during which both the atria and the ventricles are at rest.

The synchronization devices are usually based on an electrocardiogram (ECG) signal. However, the synchronization devices often cannot precisely determine the predetermined phase because 1) the heartbeats can become irregular; 2) the treatment signals themselves may cause the ECG signal to be altered; 3) the ECG signal may become noisy due to improper ECG lead placements and in from other medical devices in an operating room.

Therefore, there is a need for an improved and safer system and method for synchronizing treatment energy signals with the cardiac rhythm.

SUMMARY OF THE DISCLOSURE

According to one aspect of the present invention, a system for synchronizing application of treatment signals with a cardiac rhythm is provided. The system includes a memory and a synchronization module. The memory receives and stores a synchronization signal indicating that a predetermined phase such as R-wave of a cardiac rhythm of a patient has started. The synchronization module analyzes whether the stored synchronization signal is erroneous and if so, prevents a medical treatment device from applying a treatment energy signal such as an IRE pulse to a patient to take into account an irregular heart beat and noise in the synchronization signal in order to maximize safety of the patient.

According to another aspect of the present invention, a method of synchronizing application of treatment signals with a cardiac rhythm is provided. A synchronization signal, which indicates that a predetermined phase of a cardiac rhythm of a patient has started, is continuously received. The received synchronization signal is analyzed to determine whether it is erroneous. If so, a medical treatment device is prevented from applying a treatment energy signal, which is potentially harmful to the heart, to the patient to ensure safety of the patient.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

FIG. 18 indicates waveforms of timing diagrams indicating how the synchronization condition and synchronization problem indicators change in relation to various cardiac rhythms, most specifically referring to output for recovery from a noisy signal condition.

FIG. 19 indicates waveforms for timing diagrams indicating how the synchronization condition and synchronization problem indicators change in relation to various cardiac rhythms, most specifically referring to output for double counting of the T wave.

FIGS. 21A-B show a chart and expanded view indicating a specific mode (mode 3) of IRE energy pulse delivery contemplated for the current invention.

Figure 1:
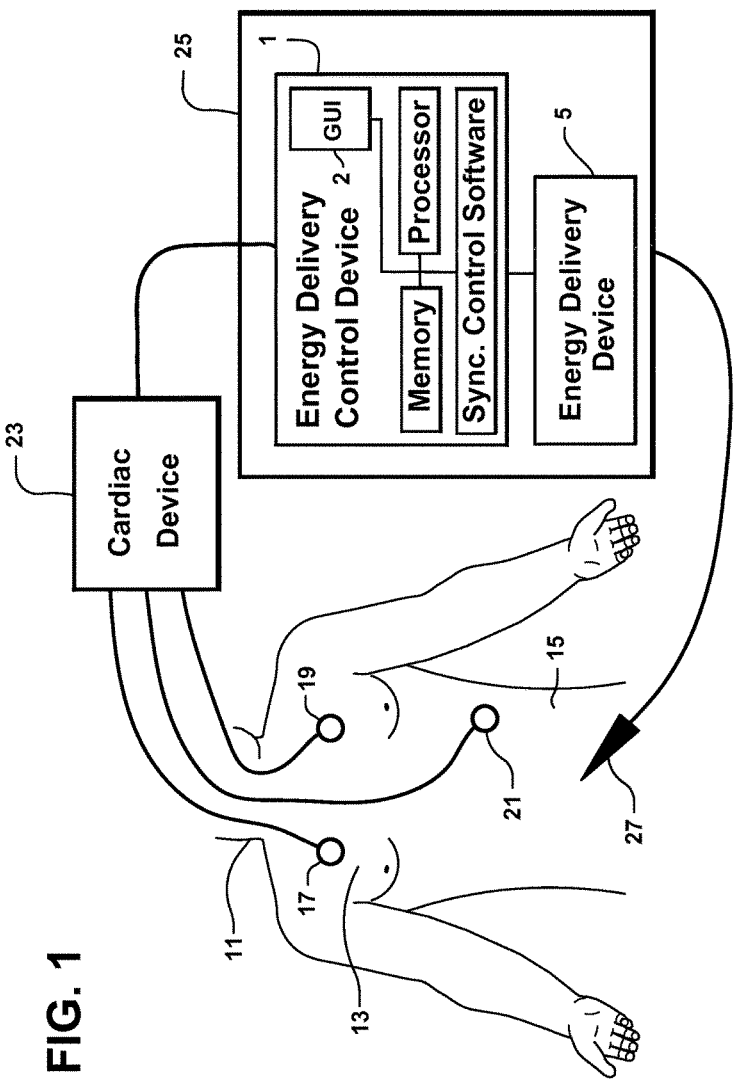
FIG. 1 depicts a treatment setup for a patient for synchronization of IRE pulse delivery with a specific portion of the cardiac rhythm.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. The full scope of the inventions is not limited to the examples that are described below.

The present invention provides a system and method involving a pulse delivery computer that will provide for application of treatment energy signals (such as IRE pulses) at specific times in the cardiac cycle such that patient safety is optimized. Herein, cardiac cycle refers to the repeatable phases of the heart such that energy release can be synchronized with specific points of those phases. It is recognized that there are mechanical and electrical aspects of the cycle, and the invention contemplates synchronization with any of the mechanical or electrical, repeatable phases of the heart. For clarity, the present invention will some times be explained in terms of delivering IRE pulses as a treatment energy signal.

The synchronization of cardiac rhythm with energy output may involve the use of medical treatment devices to release energy that can be used to ablate tissue. One example of such devices involves irreversible electroporation (IRE) technology, which is a novel methodology for ablating undesirable tissues such as cancer tissues. However, application of treatment energy signal such as IRE treatment signals to a patient potentially leads to adverse effects on cardiac function because the IRE treatment signals often involve electrical pulses of very high voltage, typically on the order of thousands of volts or more. Such high voltage pulses may potentially disrupt the cardiac rhythm. Disruption of the cardiac rhythm can lead to arrhythmias that can have dire medical consequences. The current invention provides for a energy delivery control device to release energy pulses using a flexible system that recognizes the state of the cardiac rhythm and reacts appropriately so as to provide energy release safely in a fashion currently unavailable.

As discussed above, one medical treatment device that can be used with the synchronization of cardiac rhythm is a device for applying IRE treatment signals. If properly designed, IRE is a technology that has the distinct advantage of inducing cell necrosis without causing thermal damage of tissue in the ablation zone. More specifically IRE is a technology where electrical pulses in the range of microseconds to milliseconds are applied to tissue to produce cellular necrosis and irreversible cell membrane permeabilization. IRE acts by creating defects in the cell membrane that lead to a disruption of homeostasis while sparing connective and scaffolding structure and tissue. These points have been addressed in the following publications, which are hereby incorporated by reference: Lavee J. *A Novel Nonthermal Energy Source for Surgical Epicardial Atrial Ablation: Irreversible Electroporation*. The Heart Surgery Forum. Vol. 10(2):96-101 (2007), and U.S. Patent Application Publication Number US 20060293731 A1, "Methods and systems for treating tumors using electroporation," application Ser. No. 11/165,961 filed on Jun. 24, 2005, now abandoned.

A distinct advantage of the IRE technology is the sparing of surrounding tissue, and in fact the structure of surrounding bile ducts, blood vessels, and connective tissue remains intact following application of IRE. This technology has been described in the following two patent application publications which are hereby incorporated by reference: Patent Application Publication Number WO2005/06284A2, "Tissue Ablation with Irreversible Electroporation," as well as U.S. Patent Application Publication Number US 2007/0043345A1, "Tissue Ablation with Irreversible Electroporation," application Ser. No. 10/571,162, now U.S. Pat. No. 8,048,067.

To optimize energy pulse delivery, the hardware and software relating to energy release in treatments and therapies involve coupling with a system to monitor cardiac rhythm, such as an electrocardiogram signal (ECG signal). This allows for release of energy at the proper time in a cardiac cycle. The ECG signal is used to diagnose cardiac arrhythmias through the recording and interpretation of the electrical activity of the cardiac cycle as recorded by an electrocardiograph which is a device generating the ECG signal.

The present invention can work with a wide variety of medical treatment devices and procedures. The invention can be used when the target tissue is one of the following tissues or is within the following tissues: digestive, skeletal, muscular, nervous, endocrine, circulatory, reproductive, integumentary, lymphatic, urinary, and soft tissue. The method and system can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, dysplastic, tumorous or normal. In addition, the energy delivery control device can be used for safe and efficient treatments, therapies, and ablations for patients with normal cardiac rhythms, or acute or chronic irregularities as medically reasonable, including arrhythmias, sinus arrhythmia, sinus tachycardia, sick sinus syndrome, bradycardias, premature atrial contraction (PAC), supraventricular tachycardia (SVT), Wolff-Parkinson-White syndrome, atrial flutter, atrial fibrillation, premature ventricular complexes (PVC), ventricular tachycardia (VT), ventricular fibrillation, cardiac standstill (Asystole), and various heart blocks, as well as aberrations of the atrioventricular node, the sinoatrial node, and conduction irregularities.

As background, and to establish the state of the art in certain areas of technology, applicants herein expressly incorporate by reference all of the following materials identified below in numbered paragraphs.

Mali B., Jarm T, Corovic S, Paulin-Kosir M, Cemazar M, Sersa G, Miklavic D., *The effect of electroporation pulses on functioning of the heart*. Vol. 46(8): 745-757 (2008).

Fogoros R., *Electrophysiologic Testing, 3$^{rd}$ ed.*; Blackwell Publishing, (1999).

Klabunde R, *Cardiovascular Physiology Concepts*; Lippincott Williams & Wilkins (2005).

In an example embodiment, the synchronization module maintains two indicators: a synchronization problem indicator and a synchronization condition indicator. When the synchronization problem indicator is set to logic zero, this is a representation of a normal operation, and when the synchronization problem indicator is set to logic one, this is an indication that a synchronization problem (error) exists. The synchronization problem indicator is used by the synchronization module to determine whether to allow delivery of a treatment energy signal/pulse to the patient as will be explained in detail later herein.

In the synchronization condition indicator, a setting of zero (logic state) means that too few synchronization signals (such as when an ECG lead is no longer in contact with the patient) are being received while when the synchronization condition indicator is set to logic one, this represents in this embodiment that too many synchronization signals (such as a heart rate over 120 beats per minute or in a noisy environment) are being received. Unlike the synchronization problem indicator, the synchronization condition indicator is not used in determining whether to deliver the treatment energy signals. They are only used by the GUI to display the condition of the synchronization if the synchronization problem indicator is set to high. For example, if the synchronization problem indicator is set to high and the synchronization condition indicator is set to low, the GUI may display a message that it is receiving too few signals and that it may be caused by the ECG leads being detached from the patient; on the other hand, if the synchronization problem indicator is set to high and the synchronization condition indicator is also set to high, the GUI may display a message that it is receiving too many synchronization signals which may indicate a very fast heart rate and that it may be caused by the patient under treatment.

FIG. 1 depicts a treatment setup for a patient for synchronization of energy pulse delivery with a specific portion of the cardiac rhythm. Shown is a patient with indicated neck 11, chest 13, and stomach 15 regions for perspective, along with electrocardiogram leads 17, 19, 21, a cardiac device 23 such as an electrocardiograph, and a treatment system 25 that can include an energy delivery control device 1 for synchronizing application of treatment signals with a cardiac rhythm, a graphic user interface (GUI) 2, which can be a part of the energy delivery control device and an energy delivery device 5 such as an IRE pulse generator that generates IRE treatment signals. The cardiac device 23 may be Accusync 72 ECG Trigger Monitor made by AccuSync Medical Research Corporation of Milford, Conn. Although shown for illustration purposes as a single device, the energy delivery control device 1 can comprise a synchronization control device such as Spartan-3 FPGA board with USB 2.0 made by CESYS GmbH of Germany, and a separate treatment planning computer coupled to the synchronization control device, both of which work with the GUI 2 to plan and control all aspects of a medical treatment procedure. In either case, the energy delivery control device 1 may include a memory for storing various parameters including synchronization signals from the cardiac device 23, blanking periods and various synchronization flags, a processor such as a CPU, synchronization software to be executed by the processor, and programmed logic downloaded into FPGA all working together to control the application of treatment energy signals into a patient. The memory, processor, GUI interface and sync control software are all connected to each other, for example, through a common bus. The term "synchronization module" is used herein to refer to either software or hardware or both which are required to analyze the synchronization signal and control the application of treatment energy signal based on such analysis. In one embodiment, the synchronization module comprises synchronization software and FPGA circuits that loads the software for execution. In another embodiment, the synchronization module comprises the synchronization control software and a processor as shown in FIG. 1. In one embodiment, the energy delivery device 5 comprises a high voltage pulse generator. Also shown is a set of electrodes 27 for pulse delivery to a part of the patient 15. The electrocardiograph can be a device involving one or more mechanical or electrical aspects that can include one or more computers. The output of the electrocardiograph can be on paper or digital display and can be based on a mechanical or electrical aspect or change in the heart.

Figure 2:
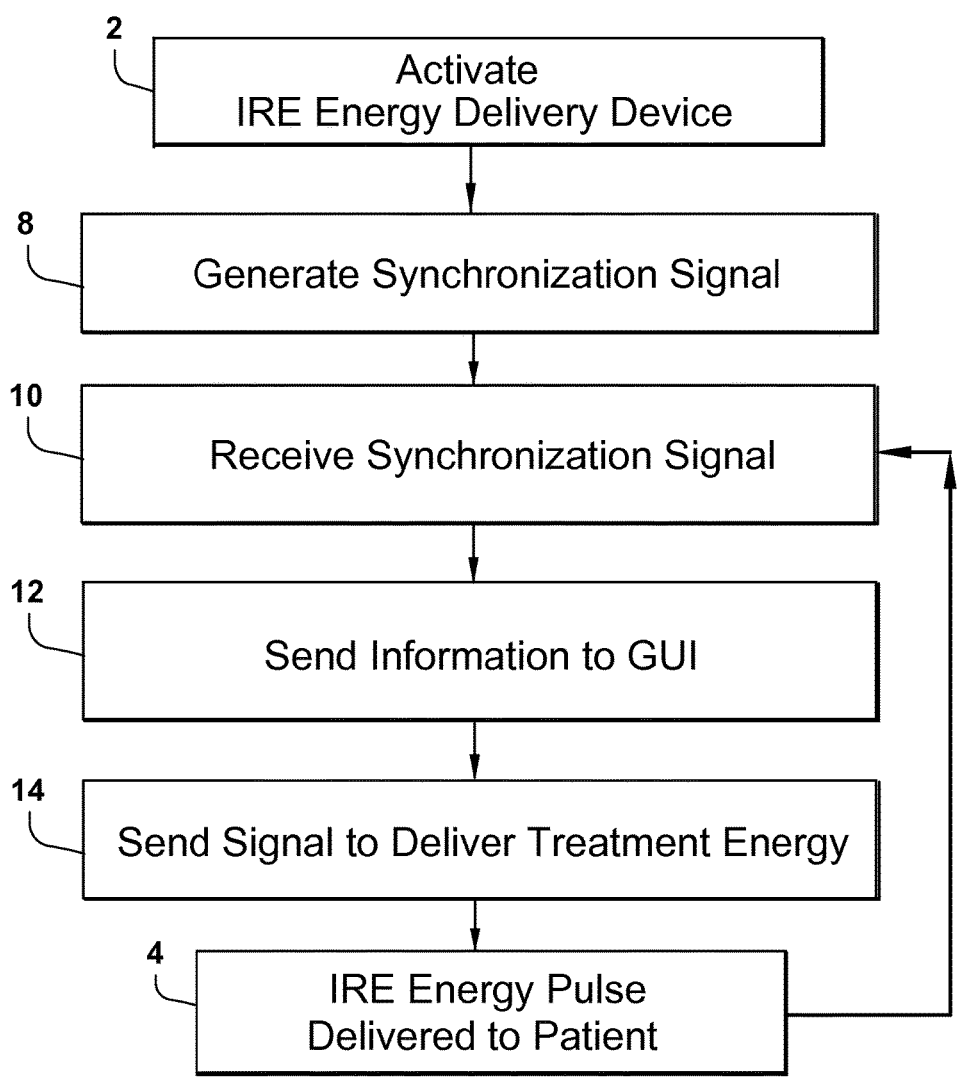
FIG. 2 depicts a flowchart showing a system for energy release to tissue of a patient.

FIG. 2 depicts a flowchart showing detailed plans for a treatment system 25 for energy release to tissue of a patient. This demonstrates the coordination between the energy delivery device 5 that releases IRE treatment energy to tissue of a patient, the cardiac device 23 that records the ECG of a patient, recognizes a specific phase of the cardiac rhythm such as an R-wave of the heartbeat and generates a continuous synchronization signal (e.g., a logic high state) indicating that the specific phase (e.g., R-wave) has started, and the energy delivery control device 1 that will receive the synchronization signal and control the timing of releasing treatment energy signals by the energy delivery device 5 (for clarity, the S wave could be a possible time for delivery of an energy pulse, but due to the fact the S wave ends nebulously in some cases, the R wave is preferably used as an indicator to start the timing of energy release). The control device 1 coupled to the energy delivery device 5 also communicates status and updates to the graphic user interface (GUI) 2 of the IRE energy unit so that they can be displayed in a display device (not shown). In various embodiments, the GUI interface 2 can be used to change one or more parameters or any of the programming of the (or related to the) energy delivery control device 1.

More specifically, the energy delivery control device 1 allows for monitoring of heart signals so as to ensure that changes, maladies, and other alterations associated with the heartbeat are coordinated such that pulses from the energy delivery device 5 are released at the proper time, and that if the heartbeat is out of its normal rhythm, that the release of energy is either altered or aborted. As will be explained in more detail later herein, in one specific embodiment, the goals of the treatment system are: 1) delivery of a first treatment energy signal soon (e.g., 50 milliseconds) after detection of the synchronization signal indicating that an R-wave of a cardiac cycle has been started and prevention of any subsequent treatment energy signal during the same cardiac cycle; 2) prevention of any treatment energy signal during a T-wave of the cardiac cycle; 3) dynamically adjusting the blanking period to account for noisy synchronization signal during which no other treatment energy signal can be delivered to the patient; 4) identification of a synchronization problem and prevention of delivering further treatment energy signals for at least the first cardiac cycle after the synchronization has been re-established; 5) abort the treatment procedure if the synchronization problem lasts for more than a certain time (e.g., more than 12 seconds).

Referring to FIG. 2, an energy delivery device 5 is activated by a physician by, for example, pressing a foot pedal to start a treatment procedure (step 2). The cardiac device 23 receives ECG information, determines the cardiac cycle stage for the patient and generates a synchronization signal indicating that a certain phase of the cardiac cycle has started (step 8). In the embodiment shown, the synchronization signal indicates that an R-wave cycle has been reached. In step 10, the energy delivery control device 1 continuously receives from the cardiac device 23 the synchronization signal. In step 12, the control device 1 sends synchronization status information to the GUI interface, where the information is displayed for users. In step 14, the control device 1 sends a signal to the energy delivery device 5 to deliver a treatment energy pulse/signal to the tissue of the patient under certain circumstances, and in step 4, the energy delivery device delivers the treatment energy to the patient. In the embodiment shown, the treatment energy signal is a single IRE pulse although the signal can comprise a sequence of IRE pulses. If more than one pulse is to be delivered, they should be delivered preferably within about 60 milliseconds of the start of the synchronization signal. The steps of 10, 12 and 14 are explained in more detail below with reference to FIGS. 3A-3C which represent the steps executed by the synchronization module within the energy delivery control device 1.

The present invention provides a system that reacts to changes in a normal cardiac rhythm, such as tachycardia or bradycardia. These changes are recognized and accounted for in the treatment energy IRE pulse delivery such that the release is still coordinated with the correct portion of the cardiac cycle, despite the change in rhythm. One way to begin to address changes in cardiac rhythms for IRE treatment energy signal release would be to dynamically adjust a blanking period programmed into the energy delivery control device 5 during which the software will prevent a pulse delivery for a set time. For example, upon receiving a synchronization signal, the software will instruct the energy delivery device 5 to deliver a first treatment energy signal to the patient and at the same time start a blanking period during which no other treatment energy is delivered. If a new synchronization signal is received by the energy delivery control device 1 during that same blanking period, subsequent treatment energy signal would not be delivered because the new synchronization signal is recognized as an erroneous signal.

Figure 3A:
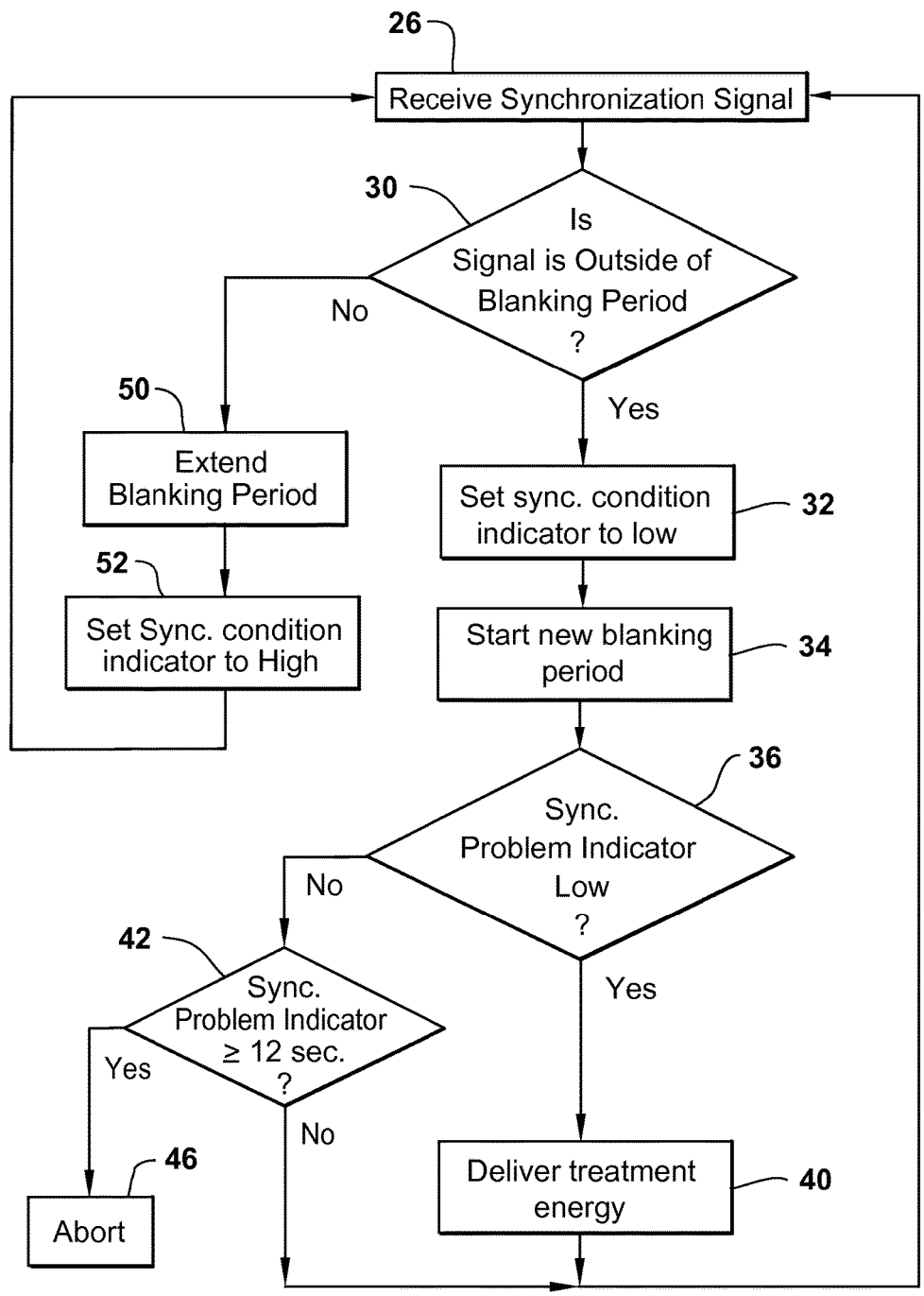
FIGS. 3A and 3B are flowcharts showing an energy delivery control device for synchronizing energy delivery to the cardiac rhythm according to the present invention.
Figure 6:
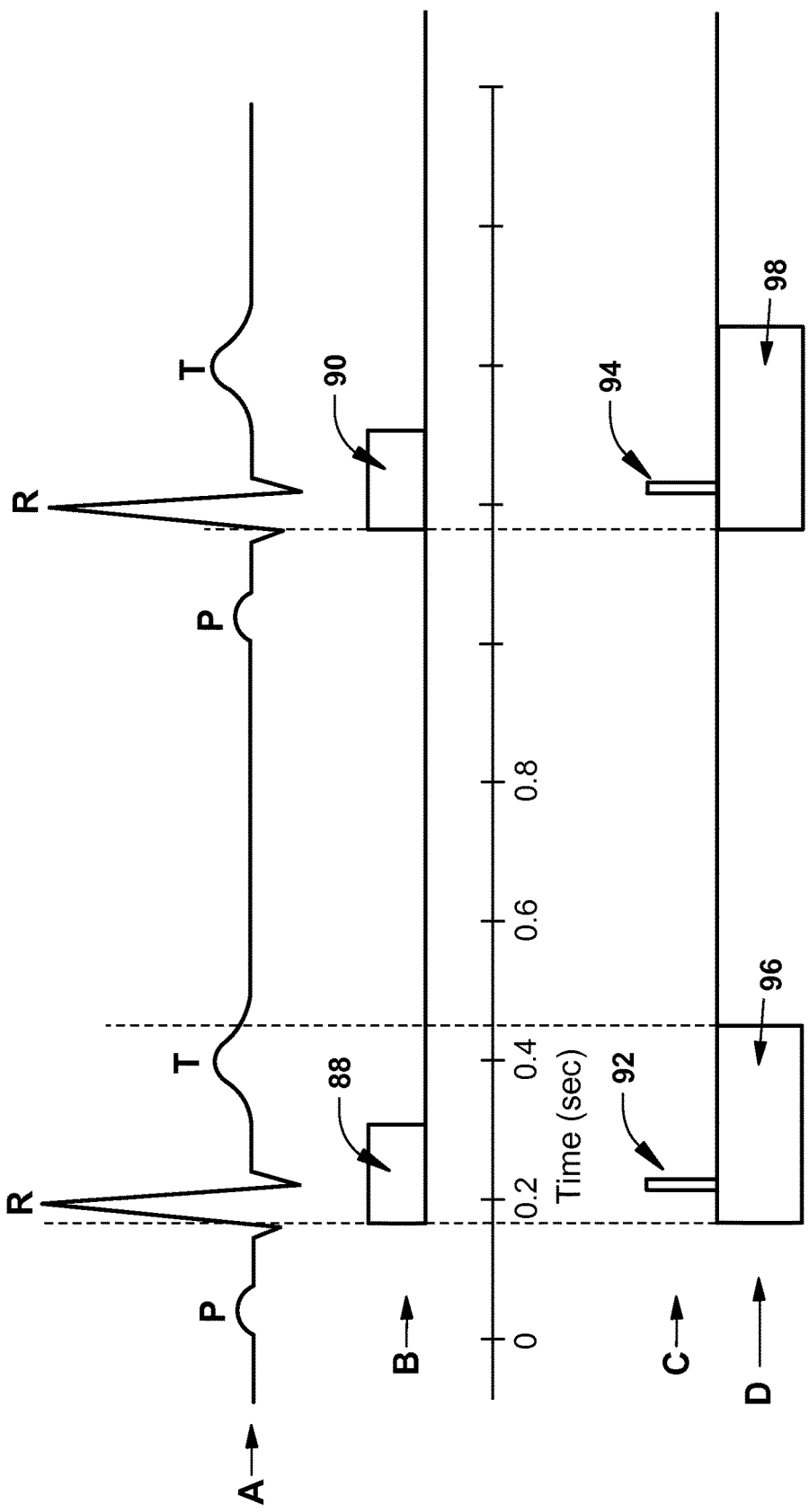
FIG. 6 shows a waveform of a normal cardiac rhythm and how the IRE pulse is released in accordance with a certain portion of that cardiac rhythm.

Referring to FIG. 3A, in step 26, the energy delivery control device 1 monitors and receives the synchronization signal from the cardiac device 23. In the embodiment shown, the cardiac device 23 analyzes electrocardiogram information, determines the stage of the cardiac cycle 24 in real-time, and generates the synchronization signal indicating that a specific phase of the cardiac cycle has been reached. In the embodiment shown, the synchronization signal is a TTL signal which indicates that the R-wave phase has been reached (see exemplary synchronization signal 88 and 90 as depicted in FIG. 6). In step 30, the synchronization module determines whether the received synchronization signal is within or outside of the blanking period which would have been set up in the previous cardiac cycle.

In the embodiment shown, the blanking period is set to 500 milliseconds although the period can vary such as from 330 to 800 milliseconds so long as the period does not include the T-wave phase of the cycle.

In a normal cardiac rhythm and if the synchronization signal is being generated correctly, then the just received synchronization signal should be outside of the previously set blanking period. If so, step 32 is executed. In step 32, the synchronization condition indicator is set to low. As discussed above, the synchronization condition indicator does not affect the determination of whether to allow the delivery of a treatment energy signal.

In step 34, a new blanking period of 500 milliseconds is started since the received synchronization signal is assumed to be part of a new cardiac cycle. In step 36, the synchronization module determines whether the synchronization problem indicator is low.

If not, that means that the synchronization module has determined that there is a synchronization problem (e.g., the received synchronization signal is determined to be erroneous) and step 42 is executed. In step 42, the synchronization module determines whether the synchronization problem indicator has been set to high for 12 seconds or more. If so, the synchronization module considers the synchronization problem as unrecoverable and aborts the medical treatment procedure in step 46. If the synchronization problem indicator has been set to high for less than 12 seconds, that means the synchronization problem is considered to be recoverable. In that case, the synchronization module goes back to step 26 where it looks for another synchronization signal. It is important to note that by going back to step 26 to look for a new synchronization signal if the decision in step 42 is no, the just received synchronization signal is ignored and no treatment energy signal is delivered. Thus, if the system is just recovering from a synchronization problem, the first synchronization signal is ignored and thereby the first cardiac cycle is ignored for purposes of delivering a treatment energy signal to the patient. In an alternative embodiment, more than one synchronization signal (e.g., three synchronization signals) an be ignored before the treatment energy signal is delivered again.

Referring back to step 36, if the synchronization module determines that the synchronization problem indicator is low, it means that synchronization is being maintained and step 40 is executed. In step 40, the synchronization module in the control device 1 waits for a predetermined time period (e.g., 50 milliseconds) after the synchronization signal has been received (e.g., starting from the leading edge to logic high) and sends a signal to the energy delivery device 5 to apply the treatment energy signal (see exemplary pulse 92 within the blanking period 96 in FIG. 6). In the embodiment shown, the treatment energy signal is a single IRE pulse of 100 microseconds although a set of pulses can be applied so long as they are not applied during the T-wave phase. Waiting for 50 milliseconds ensures that the treatment energy is applied at an optimal time (e.g., during the refractory period).

Once the synchronization module sends the instruction to apply the treatment energy signal, no more treatment signals are allowed within the remaining blanking period. If a new synchronization signal is received within that same blanking period, it will be rejected as being erroneous and the current blanking period will be dynamically adjusted by another 500 milliseconds from the time the new synchronization signal is received. During the extended blanking period, no new treatment energy signal is allowed to be delivered as will be explained below.

If in step 30, the synchronization module determines that the synchronization signal was received within the current blanking period, this is indicative of cardiac rhythm irregularity and the blanking period will be extended in step 50. See exemplary blanking period in FIG. 10 where the original blanking period 144 has been overlapped with a new blanking period 146 to extend the blanking period in which no new treatment signal can be delivered until the end of the blanking period 146. In step 52, synchronization condition indicator is set to high to indicate that too many synchronization signals are being received. As discussed above, this may indicate a rhythm problem, noise, a loose pad or wire, or ECG double counting. Once step 52 is executed, the synchronization module returns to step 26 where it waits for a new synchronization signal.

In the case of tachycardia, the heart rate by definition is over 120 beats per minute. If the 500 ms blanking period is used, this will cause the blanking period to be dynamically adjusted indefinitely. So, a shorter blanking period should be used.

Figure 3B:
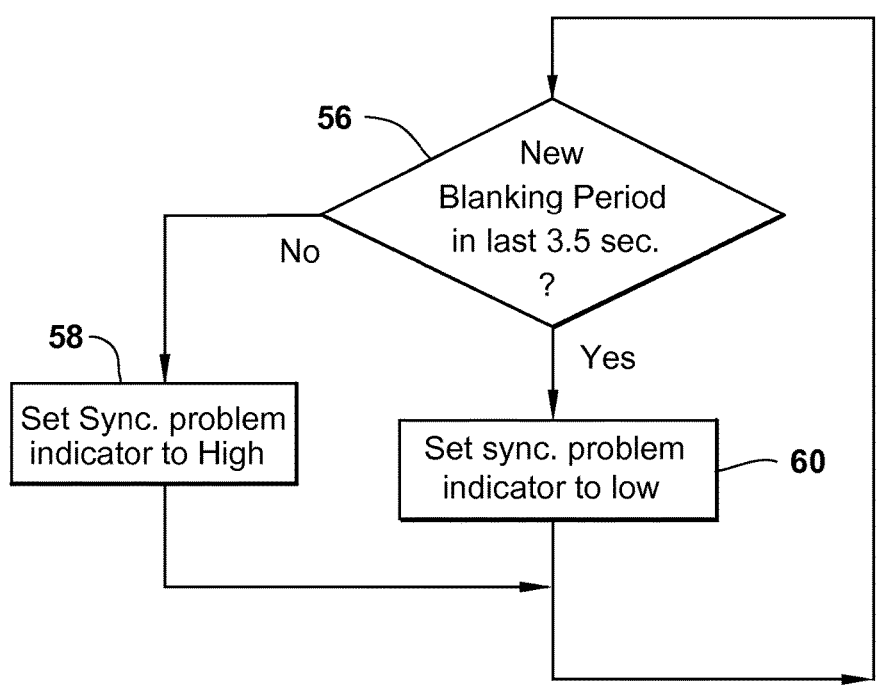

FIG. 35 illustrates a flowchart of a set of steps that are executed by the synchronization module independently of those in FIG. 3A to determine whether the synchronization signal is erroneous. In other words, the steps of FIG. 3A and FIG. 3B are executed concurrently within the synchronization module of the control device 1. In step 56, the synchronization module continuously determines whether a new blanking period has begun within the last 3.5 seconds (the new blanking period is started in step 34 of FIG. 3A). If so, the synchronization problem indicator is set to low in step 60. However if there has been no new blanking period within the last 3.5 seconds, the synchronization problem indicator is set to high. This may mean either that no synchronization signals are being received or that too many are being received to continuously extend the current blanking period (see continuously extending blanking period E in FIG. 10, for example). In that case, the synchronization module sets the synchronization problem indicator to high in step 58 to indicate that the synchronization signal is received in error. After executing either step 58 or step 60, the synchronization module returns to step 56 to check for the new blanking window in order to constantly update the synchronization problem indicator.

Although the control device 1 has been described with reference to an R-wave, it can also use other phases of the cardiac cycle such as the T-wave such that the control device prevents the firing of a treatment energy signal to the patient during the T-wave phase in that case, the cardiac device 23 will generate a synchronization signal that indicates that a T-wave of a cardiac cycle has been started and the same steps can be performed to dynamically adjust the blanking period, except that no treatment energy will be applied during the T-wave phase. Alternately, the control device can be adapted to prevent the delivery of a treatment signal for a fixed period of time after every occurrence of the synchronization signal indicating that a T-wave phase has been started.

Figure 4A:
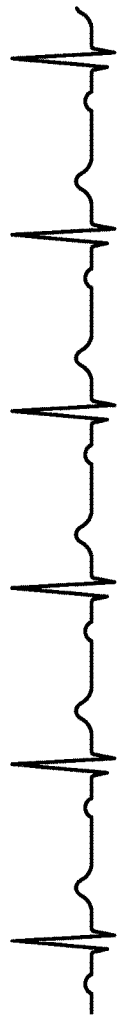
FIGS. 4A, 4B and 4C depict an ECG waveform for a healthy adult.
Figure 4B:
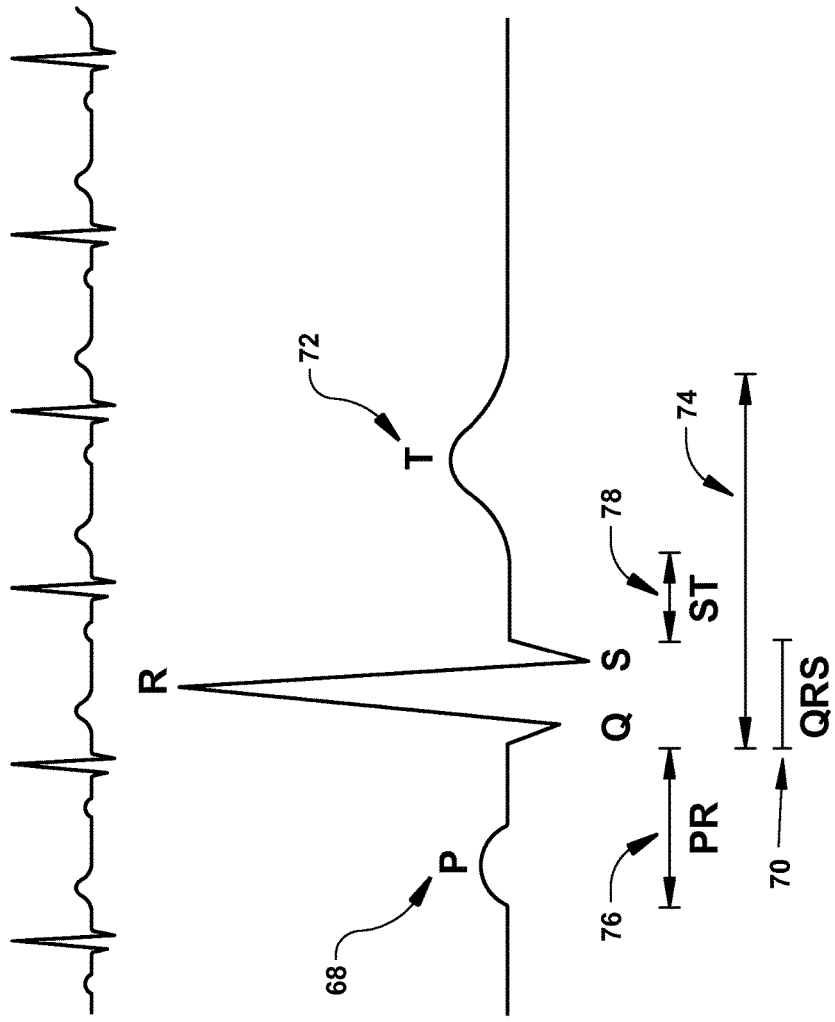
Figure 4C:
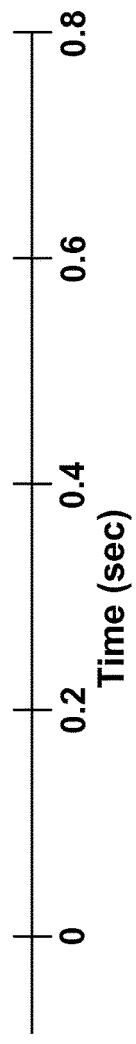

FIGS. 4A-4C depict an ECG waveform for a healthy adult. FIG. 4A shows a normal waveform for approximately 6 heartbeats. FIG. 4B shows a single normal cardiac ECG reading. Specifically shown are the P, Q, R, S, and T portions of the cardiac cycle. The P-wave 68 indicates atrial depolarization that leads to contraction. The QRS complex 70 shows ventricular depolarization that leads to contraction. The T-wave indicates ventricular repolarization 72. Indicated for completeness are the QT interval 74, PR segment 76 and the ST segment 78. FIG. 5C shows normal ECG segment for a healthy adult. The P-wave 68 is generally 80-100 ms, the QRS complex 70 is approximately 60-100 ms, and the QT interval 74 is 200-400 ms.

Figure 5:
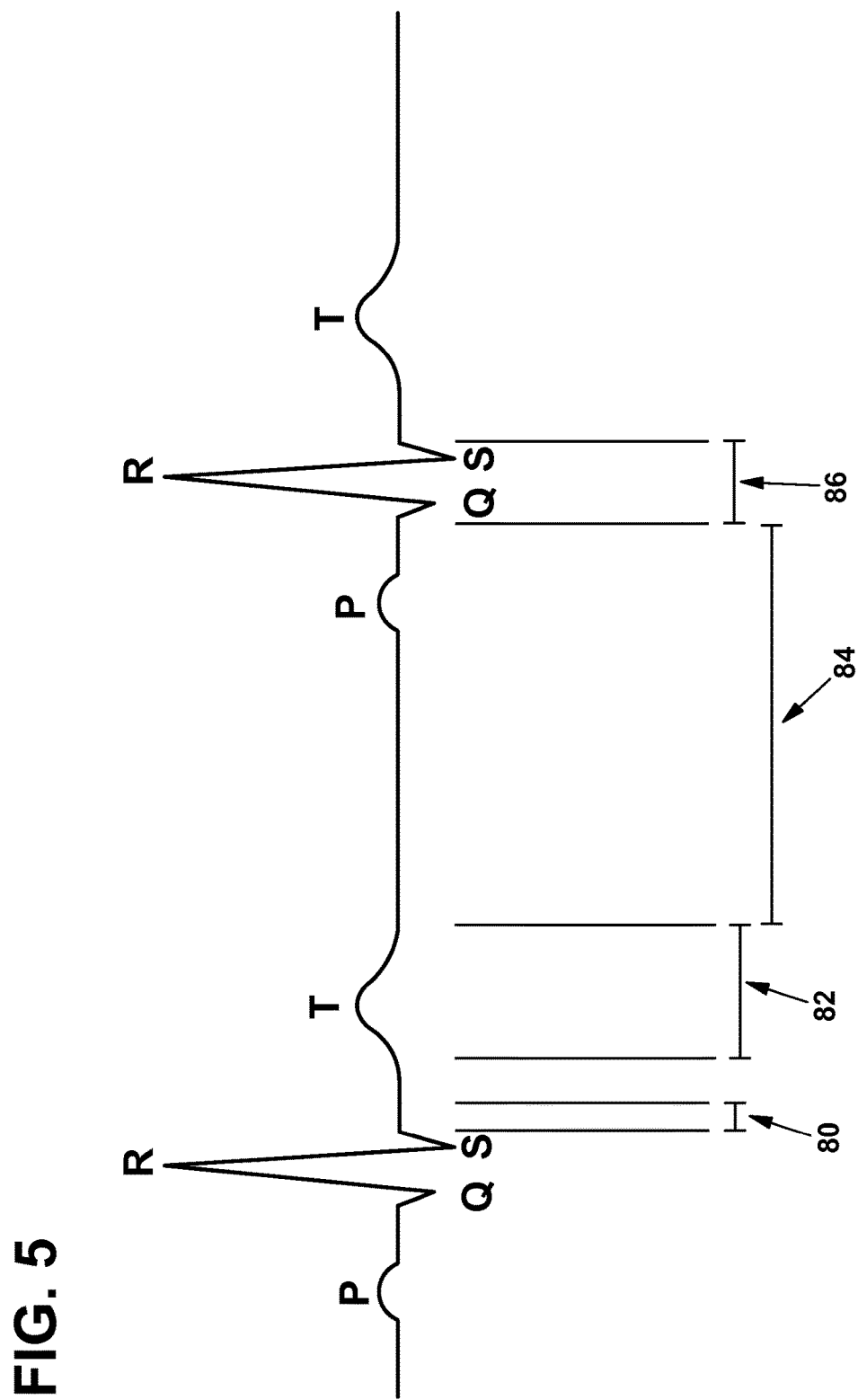
FIG. 5 shows a waveform of the ECG in relation to when energy should be released for treatment.

FIG. 5 shows a waveform of the ECG in relation to when energy for treatment should be released. This shows the preferred 80 (e.g., refractory period) and possible 86 points of the cardiac cycle to release energy for treatments, along with a time where energy should not be released 82 (T-wave portion), and a time where energy release could cause pacing 84. Energy release at 80 will not affect the cardiac rhythm due to the status of depolarization. Energy release at 86 also can be used for release of energy in treatment though through that range some depolarization is occurring. Energy release at 84 could affect heart rate and rhythm and can be used by experts in very specific cases to advance treatment of patients. Energy release at 82 could cause cardiac rhythm irregularities.

FIG. 6 shows a waveform (A) of a normal cardiac rhythm and how the IRE pulse is released in accordance with a certain portion of that cardiac rhythm. Typically the IRE therapy is delivered within the refractory period so that the IRE pulse is matching the depolarized state of the heart. In one embodiment, the IRE energy delivery unit has built in blanking periods 96, 98 (in this example each blanking period is 330 ms) activated when it receives a synchronization signal (B) 88 and 90 corresponding to synchronization signals indicating electrocardiogram electrical signals relating to two heartbeats, respectively. Once the IRE pulse (C) is delivered for a particular blanking period (D), additional synchronization signals received during the same blanking period are disregarded. In this case the electrical signals A for two heartbeats are shown as are the released IRE pulses 92, 94 associated with the electrical signals relating to those two heartbeats.

Figure 7:
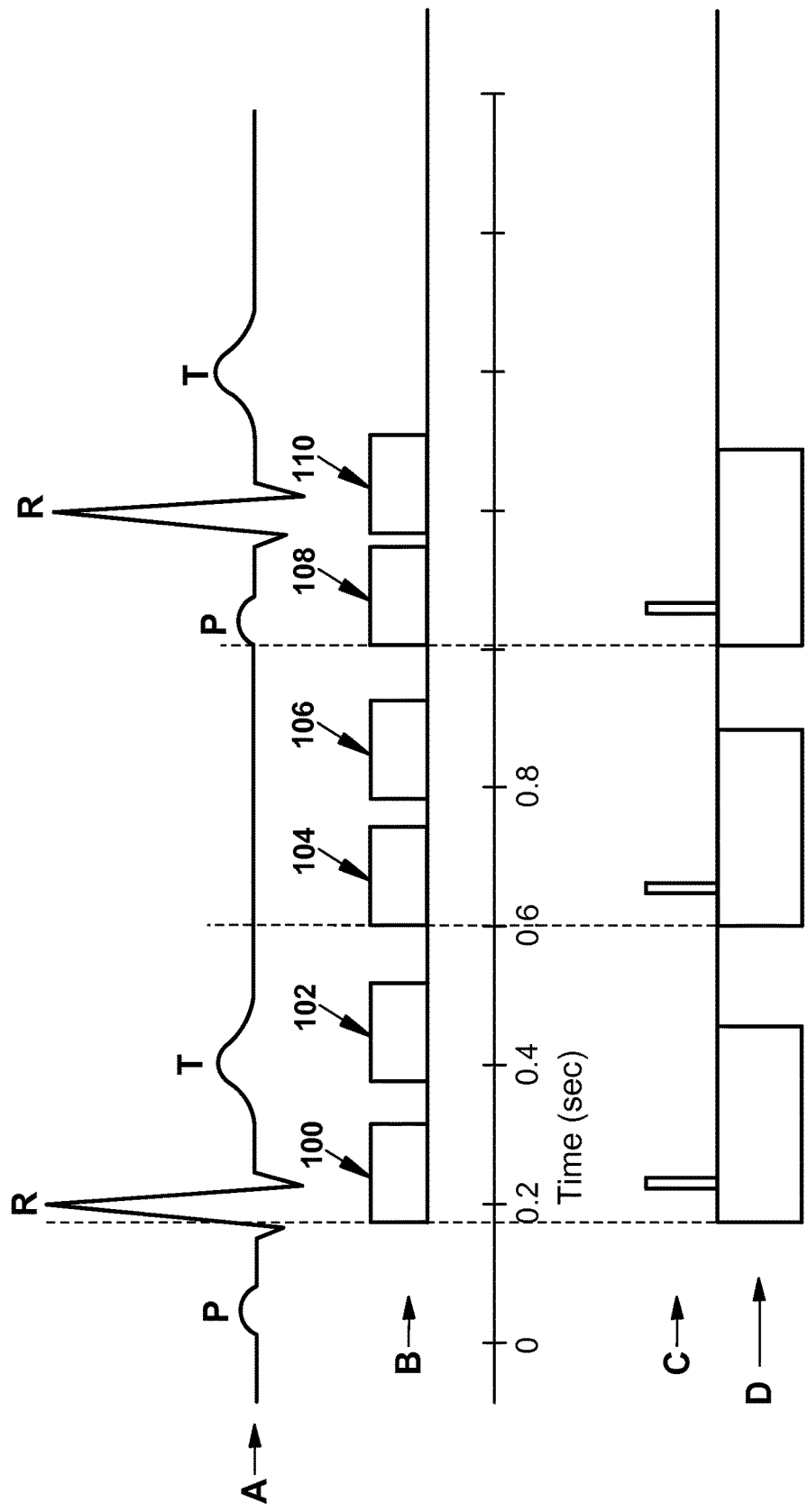
FIG. 7 shows a waveform including a depiction of IRE treatment for a normal QRS rhythm in a noisy environment where the synchronization signal indicates more than 1 R-wave.

FIG. 7 shows a waveform including a depiction of IRE treatment for a normal QRS rhythm in a noisy environment where the synchronization signal (such as from an Accusync device sending a signal or trigger) indicates more than 1 R-wave within a single cardiac cycle. The six synchronization signals are shown as 100, 102, 104, 106, 108, and 110 respectively. There is a need in the art for devices that will monitor and react to conditions such as this, beyond just a blanking period. For systems that have a set blanking period and are not reactive, what will happen in a situation such as this is the following: signal 100 will lead to a proper IRE energy pulse and the second synchronization signal 102 (since the leading edge is in the blanking period) will be ignored, and signal 104 will lead to an IRE energy pulse that is released at the wrong time. Signal 108 will be ignored by the system (as it is in a blanking period), signal 108 will cause an IRE pulse release at the wrong time, and signal 110 will be ignored since it is in the blanking period). With systems that are improperly activated in a noisy environment, incorrect signals for pulse release can lead to more than 180 IRE energy pulses per minute that are not synchronized with the R-wave.

Figure 8:
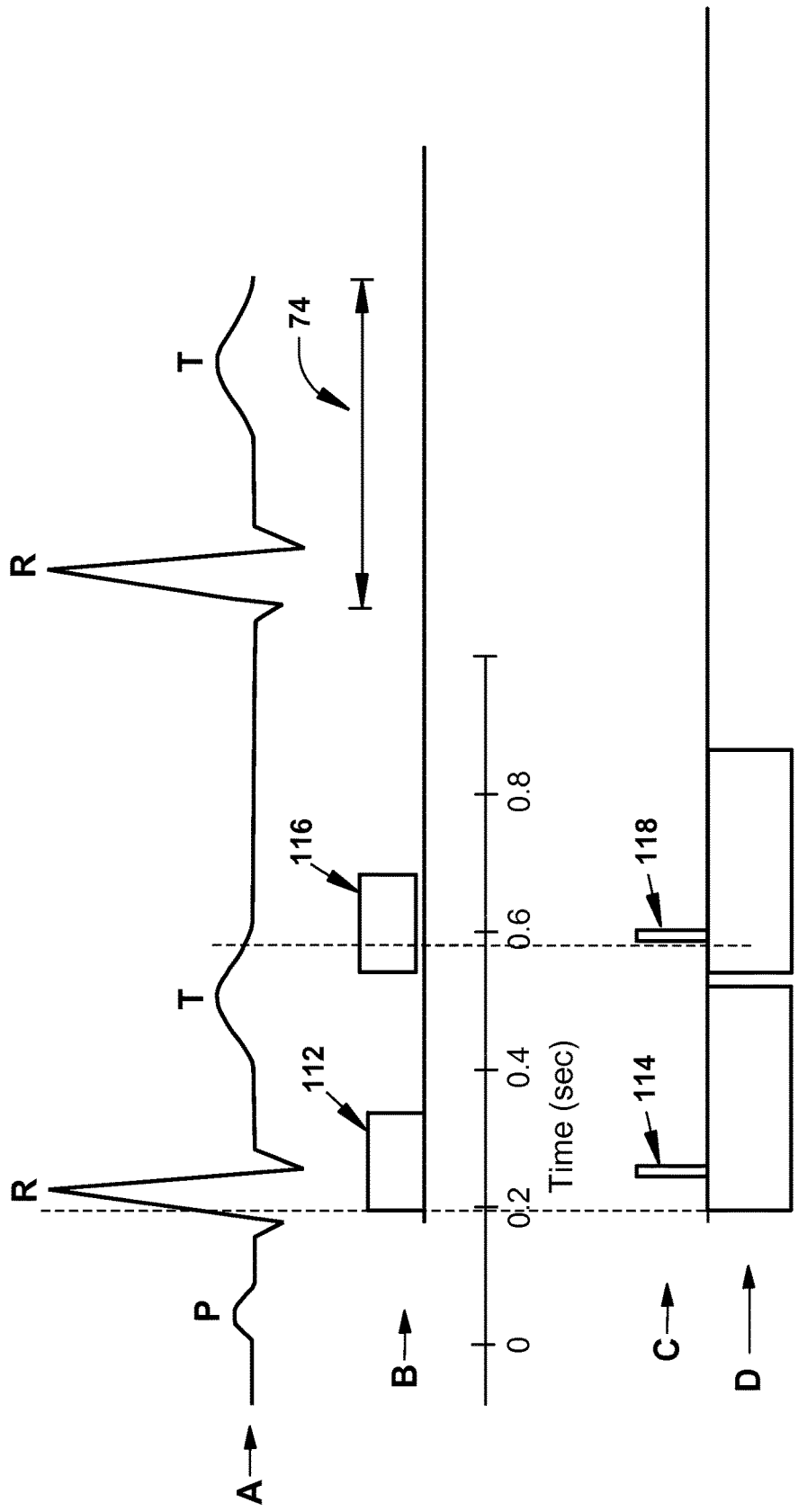
FIG. 8 shows a waveform including a depiction of synchronization signaling when the QRS segment is at the long range of normal.

FIG. 8 shows a waveform including a depletion of synchronization signaling when the QRS segment 70 is at the long range of normal. A QT 74 interval of 400 ms is at the long limit of normal. For systems that have a set blanking period and are not reactive, what will happen in a situation such as this is the following: shown in FIG. 8 is a synchronization signal at the proper time 112 and the proper IRE energy pulse release 114, and a second signal 116 that comes at the incorrect time. Incorrect signals can cause unsynchronized IRE energy pulses, such as after the second synchronization signal 116 that leads to an IRE energy pulse release 118 on the T-wave. An IRE pulse at this time can lead to at least one abnormal cardiac contraction. In one example, if the time from one R wave to another R wave is 1000 milliseconds, then there is 2% chance that the IRE energy pulse would be delivered during the T-wave (since the vulnerable T wave portion would be 20 milliseconds and the released pulse would have a 20/1000 or 2% chance of being delivered at that incorrect time).

Figure 9:
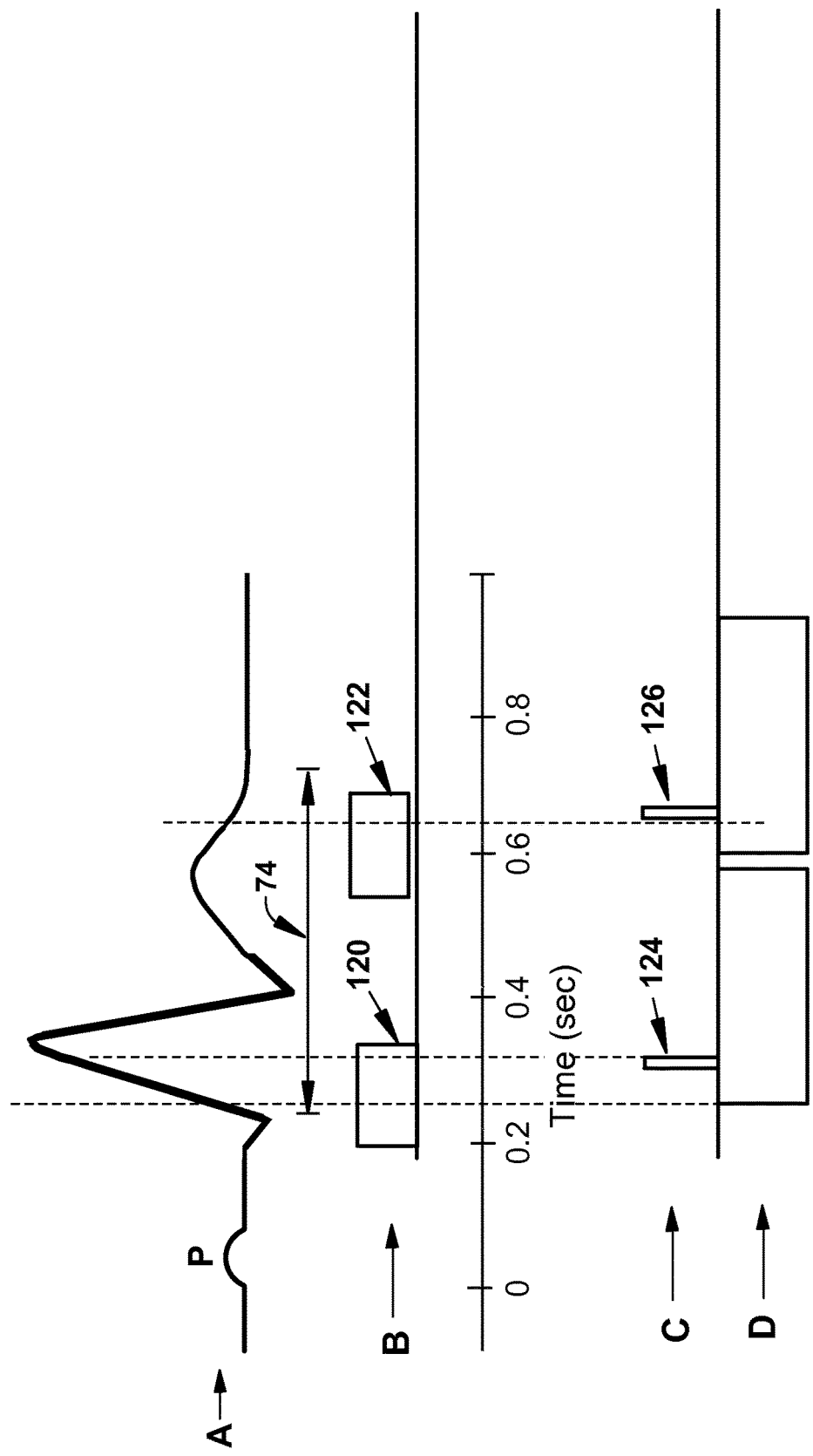
FIG. 9 shows a waveform including a depiction of synchronization signaling when there are ventricular conduction problems such as an abnormally long QRS segment.

FIG. 9 shows a waveform including a depiction of synchronization signaling when there are ventricular conduction problems such as an abnormally long QRS segment. Shown in FIG. 9 are: the QT segment 74, two synchronization signals 120 and 122, and two corresponding IRE energy pulses (124, 126). For systems that have a set blanking period and are not reactive, what will happen in a situation such as this is the following: In this case the QT segment 74 is longer than normal. The first synchronization signal 120 leads to a proper IRE energy pulse release 124. The second synchronization signal comes during the T wave at an improper time and in this example leads to an improper IRE energy pulse release 126. More generally, a QT interval of 500 milliseconds would be an example of the QT segment indicated in FIG. 7. This can occur with Left Bundle Branch blocks or in cases of Dilated Cardiomyopathy. The situation is similar to when the QT interval is 400 milliseconds except that the window where an IRE energy pulse can be released during a T wave becomes greater (such as 120 milliseconds). In an example case random noise could have a 120/1000 or 12% chance of causing an IRE energy pulse release during a T wave. A properly synchronized IRE pulse will land on the QRS complex and can create an abnormal contraction with reduced or with no cardiac output. In general, patients with a history of structural heart disease are at a significantly higher risk for reentrant ventricular tachyarrythmias than the general population. In such cases IRE energy pulse releases during the T wave would be likely to lead to a sustained dangerous cardiac arrhythmia. In current embodiments of the described invention herein, the IRE pulse delivery computer is coupled to computer databases and patient databases so that records and archives can be reviewed (by the IRE pulse delivery computer or a computer or one coupled to it) to obtain and analyze an individual patient's history and likelihoods as well as a population's history and likelihoods. The computer can also be coupled to computers and databases for retrieval and analysis of statistics and medical therapies and recommendations.

Figure 10:
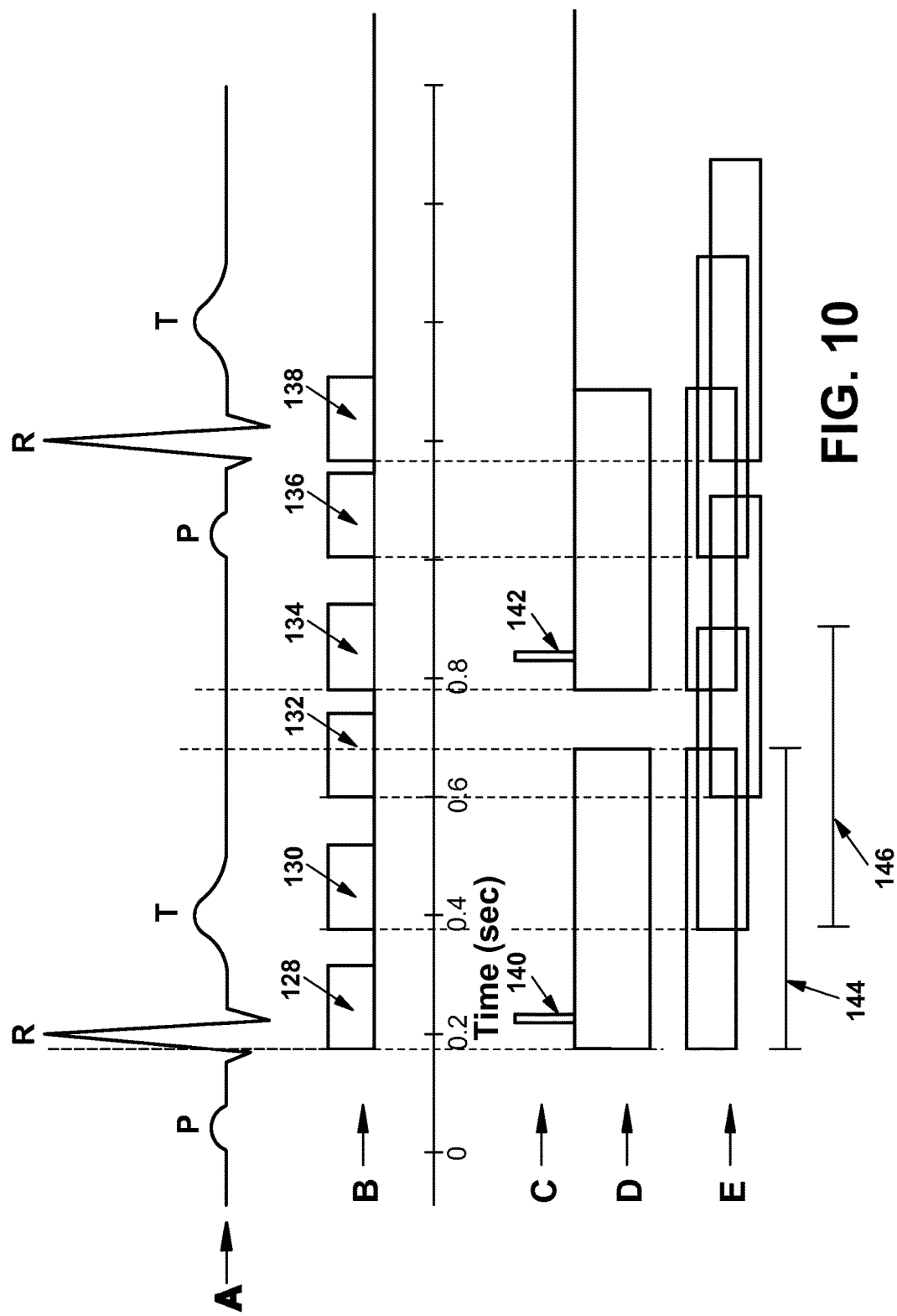
FIG. 10 shows a waveform including a depiction of synchronization signaling ere there is a normal QRS segment in a noisy environment.

FIG. 10 shows a waveform including a depiction of synchronization signaling where there is a normal QRS segment in a noisy environment. FIG. 10 shows an advantage of the current invention, which prevents unsafe IRE energy pulse release by providing for the recognition of pulses that occur within a given blanking period and allows for a retriggering of the ongoing blanking period. In other words, if a synchronization signal is received during a blanking period, then in recognition of the fact this is indicative of a dysrhythmia, then the blanking period will be extended so as to account for this disruption. More specifically, FIG. 10 shows six synchronization signals 128, 130, 132, 134, 136, and 138. In a situation where a set blanking period has been put in place, this will lead to two IRE energy pulse releases (140 and 142), however as in this example, the release of the second IRE pulse can be at an undesirable time that can adversely affect cardiac function. One advantage of the current invention is that a blanking period can be extended when synchronization signals are received during the blanking period. In other words if there was a 500 millisecond blanking period starting at time zero, and a signal was received at 250 milliseconds, then at that 250 millisecond point, the blanking period would be extended an additional 500 milliseconds (for a total of 750 milliseconds from time zero). Using this system, then the 6 synchronization signals in FIG. 9, 128, 130, 132, 134, 136, and 138 would only lead to the first and proper IRE energy pulse release. FIG. 10 shows a normal blanking period 144, and an overlayed, extended blanking period 146.

Figure 11A:
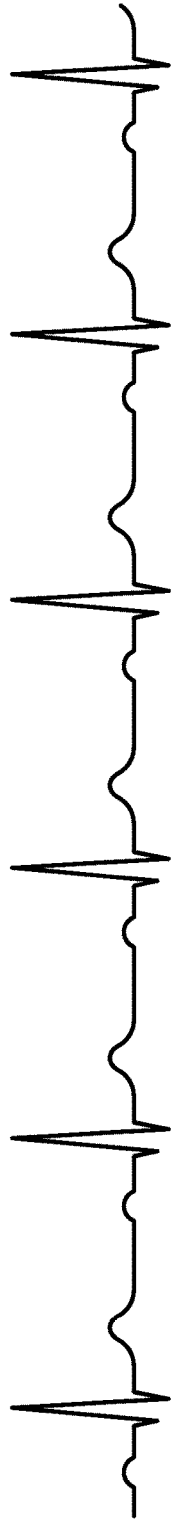
FIGS. 11A, 11B, and 11C show an electrocardiogram waveform of a normal sinus rhythm and of IRE energy pulse release as associated with arrhythmias.
Figure 11B:
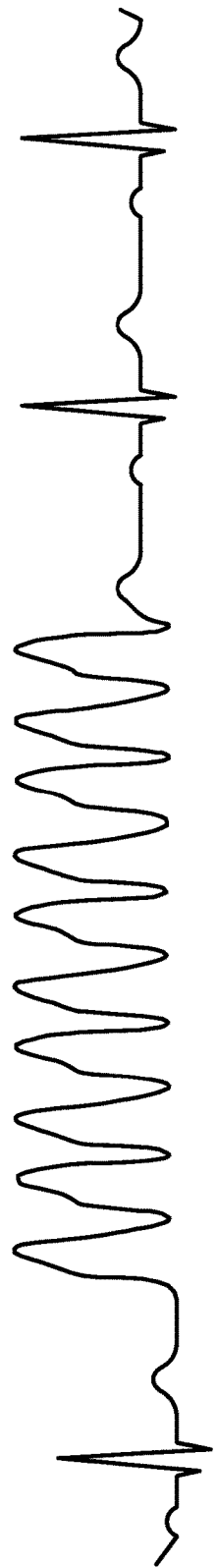
Figure 11C:
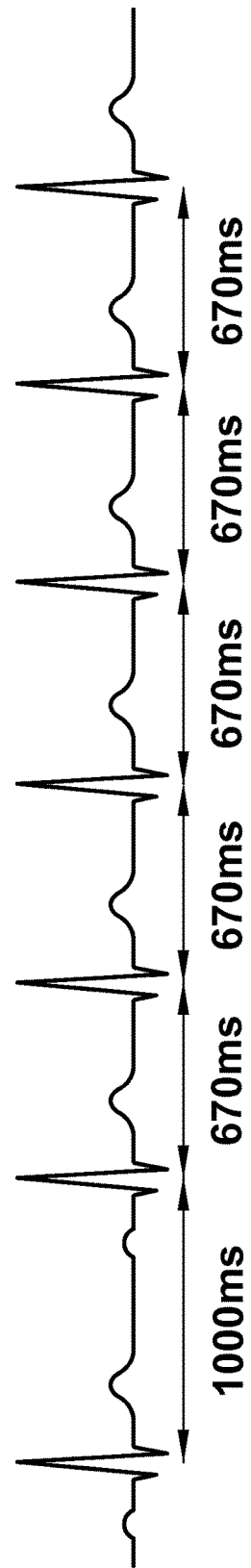

FIG. 11 shows an electrocardiogram waveform of a normal sinus rhythm and of IRE energy pulse release as associated with arrhythmias. FIG. 11 shows an example of the current invention where if necessary, IRE release can affect the sinus rhythm (in situations where electrocardiogram synchronization is not available). More specifically, FIG. 11A shows a normal sinus rhythm (NSR). In comparison, FIG. 11B shows a situation where there is transient arrhythmia (ventricular flutter that can be 240 beats per minute, where cardiac output drops or goes to zero and sustained tachyarrythmia is possible). Tachyarrythmia can occur spontaneously and could potentially occur if IRE pulses were delivered at inappropriate times and therefore affected cardiac depolarization. By contrast, FIG. 11C shows a situation where the heart rhythm has been affected by energy release, as energy release for electroporation can be used to pace the heart. In various embodiments energy release is performed as all or part of a patient treatment where the patient may have an irregular or normal cardiac rhythm, and in those embodiments, treatment indicates an action to benefit the patient condition.

Figure 12A:
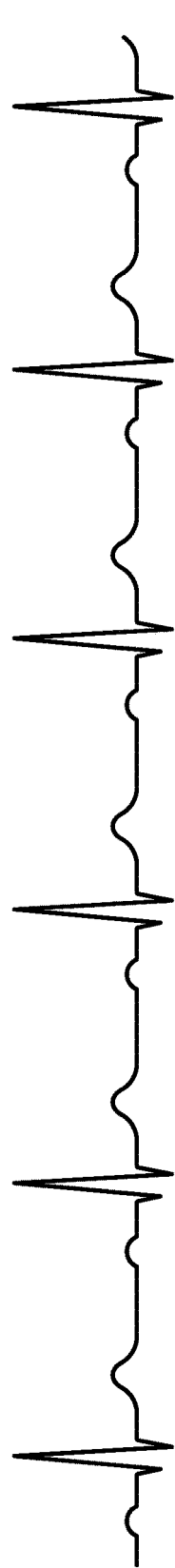
FIGS. 12A-B show a waveform outline of a normal sinus rhythm and a cardiac arrhythmia known as bradycardia.
Figure 12B:
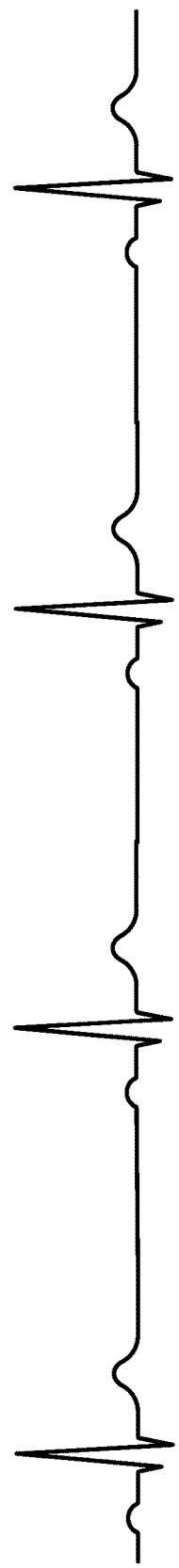
Figure 13A:
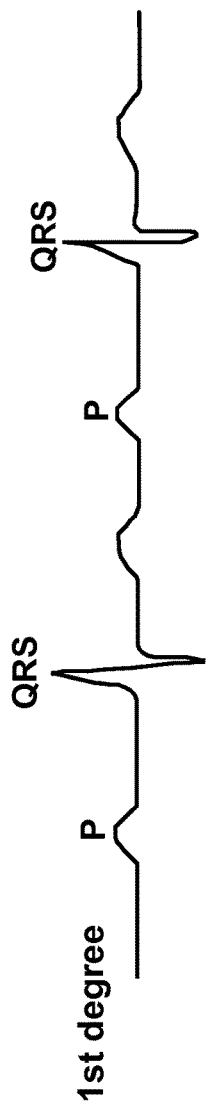
FIGS. 13A, 13B, and 13C show waveforms of problematic, first, second, and third degree conditions of bradycardia.
Figure 13B:
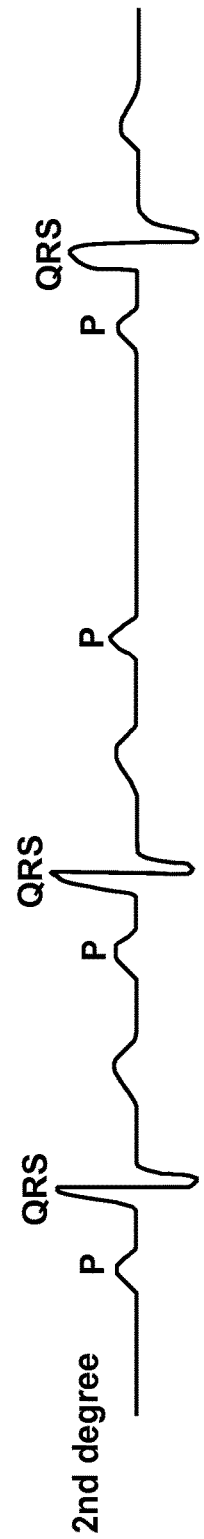
Figure 13C:
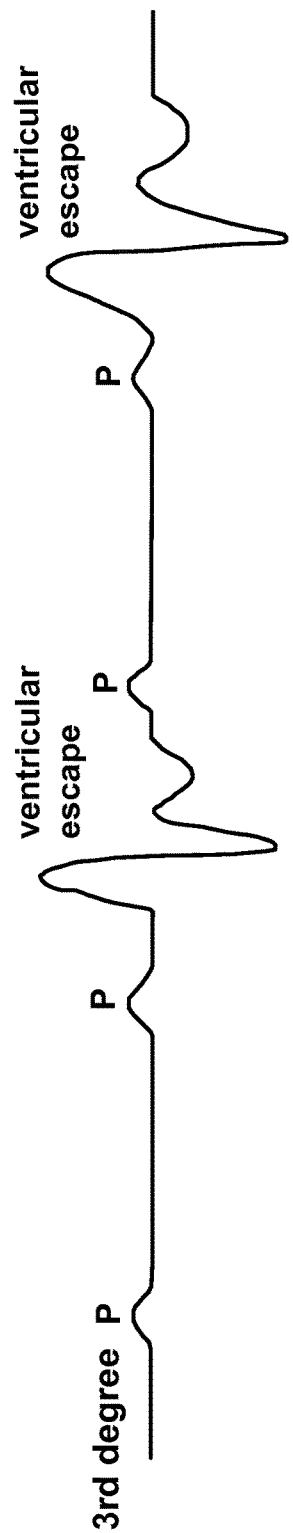
Figure 14:
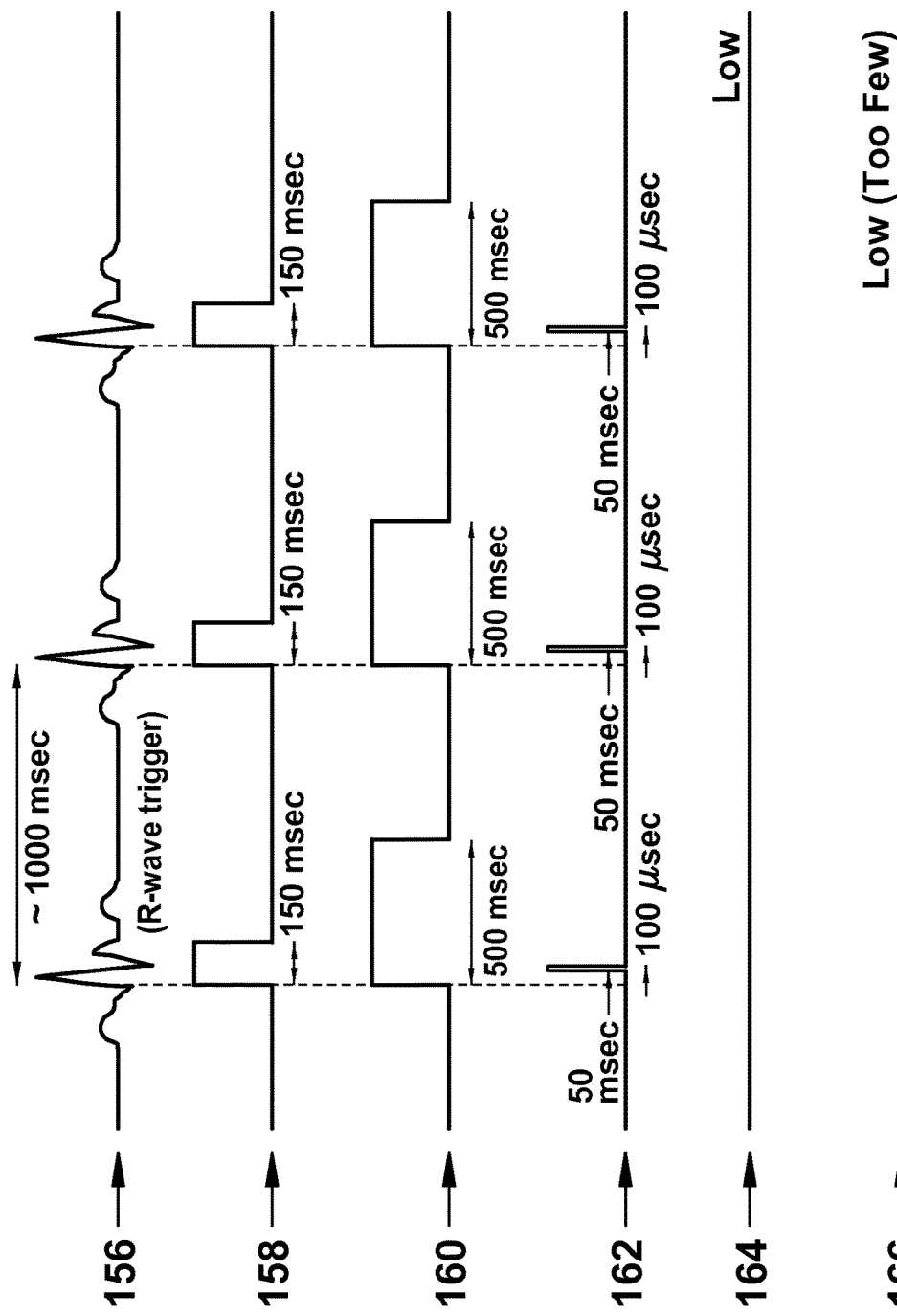
FIG. 14 shows waveforms that indicate a potential display within an embodiment of the current invention showing a cardiac rhythm, output from a synchronization device, output showing blanking, the IRE energy pulse release, and an output showing a synchronization problem and synchronization condition.

FIGS. 12 and 14 show waveforms that outline a cardiac arrhythmia known as bradycardia that is to be accounted for in the IRE energy pulses system. Specifically FIG. 12A shows the normal sinus rhythm, and FIG. 12B shows a slower heart rate (bradycardia). There is a long duration between the P waves. Patients can normally be treated in normal IRE synchronization mode. FIG. 13 shows problematic bradycardias where these arrhythmias indicate underlying conduction problems. FIG. 13A shows an example of first degree bradycardia, FIG. 13B shows second degree bradycardia, and FIG. 13C shows third degree bradycardia. Ideal IRE energy release systems will recognize changes in the cycle such that IRE pulses are not released at an inappropriate portion of the cycle.

FIG. 14 shows waveforms that indicate a potential display within an embodiment of the current invention showing a cardiac rhythm 156, output from a energy delivery control device 158 (shown as Accusync in this example), output showing blanking 160, the IRE energy pulse release 162 (shown here as treatment), and an output showing a synchronization problem indicator 164 and synchronization condition indicator 166. Each of 164 and 166 represent indicators or internal mechanisms to demonstrate on the graphic user interface that there has been a change or is an aberrant cardiac rhythm in which to take into account for optimal IRE energy pulse release. These indicators are part of the energy delivery control device demonstrated in FIGS.

4-6. In certain embodiments of the energy delivery control device, the Accusync synchronization device is used, synchronization output is generated on every R-wave, the patient has a normal rhythm morphology, the RT interval is less than 500 ms, and the anesthetized heart rate is 50-70 beats per minute.

Table 1 below, shows a chart indicating embodiments indicating multiple modes of IRE energy pulse delivery contemplated for the current invention.

TABLE 1

| Delivery Mode | Description | When Used |
|---|---|---|
| Mode 1 - ECG Synchronized (Default Mode) | 3rd Party synchronization (cardiac) device generates a sync signal on patient R-wave. Energy delivery device delivers IRE pulse 50 ms after sync signal. | Thoracic or abdominal locations (liver, lung, pancreas). |
| Mode 2 - Low rate, Not ECG Synchronized | Energy delivery device delivers 90 IRE pulses in trains of 10 pulses each. 670 ms between (90 pulses/min) and 3.5 seconds between trains | Only if sync problems prevent treatment. |
| Mode 3 - High rate, Not ECG Synchronized | Energy delivery device delivers 90 IRE pulses in trains of 10 pulses each. 250 ms between pulses (240 pulses/min) and 3.5 seconds between trains. | Prostate. (Plus other distal locations in the future). |

Mode 1 is an electrocardiogram synchronized mode where a third party synchronization device generates a synchronization signal on the patient R-wave. An IRE energy delivery device delivers an IRE pulse 50 ms after the synchronization signal. Mode 1 can be used for many IRE energy pulse release locations, including but not limited to thoracic, abdominal, liver, lung, and pancreas. Table 1 also shows a second mode; mode 2 involves a low cardiac rate, not electrocardiogram synchronized. An IRE energy pulse device delivers pulses. In certain embodiments the release involves 90 pulses in trains of 10 pulses each (where a train is consecutive pulses released), and were there are 670 ms between pulses, and 3.5 seconds between trains of pulses. Mode 2 can be used if synchronization problems would otherwise prevent treatment. Table 1 also shows a third mode; mode 3 involves a high cardiac rate, not electrocardiogram synchronized. An IRE energy pulse release device delivers pulses. In certain embodiments 90 pulses are released in trains of 10 pulses each, with 250 ms between pulses (240 pulses per minute) and 3.5 seconds between trains. Mode 3 can be used, among other options, to treat prostate and areas and regions adjacent to the prostate. In various embodiments the moment for energy release for ablation is determined from the peak of the R-wave, and in other embodiments it is determined from part of the slope of the R-wave prior to or following the peak of the R-wave. In various embodiments the moment for energy release is determined in relation to when the R-wave has reached ⅓ of its ultimate peak height on the ECG reading, and on other embodiments, the energy release is determined in relation to when the R-wave has reached ⅔ of its ultimate peak height on the ECG reading. The readings and calculations (involving determinations for energy release) and visual display of results can be performed in real-time.

FIGS. 15-19 indicate waveforms of timing diagrams indicating how the synchronization condition and synchronization problem indicators change in relation to various cardiac rhythms. In certain example embodiments of the invention, the terms Cardiac 156, Accusync 158, Blanking 160, Treatment 162, Sync Problem 164, Sync Condition 166, and Sync Status 168 refer to the following: 1) Cardiac: the 3 lead surface electrocardiogram seen by a synchronization device, 2) Accusync: a synchronization device that is a 5 Volt transistor transistor synchronization (TTL)—signal output by Accusync that is 150 ms long, 3) Blanking is an internal 500 ms blanking period programmed into software associated with the Energy delivery device 5 (such as NanoKnife® IRE System from AngioDynamics of Latham, N.Y.)—where the blanking starts with each synchronization signal and during an active blanking period synchronization signals do not trigger an IRE pulse, 4) Treatment: Output from the energy delivery device, 5) Sync Problem—(Synchronization problem)—an internal indicator in the stored in the memory of the control device 1 that is normally in the low state, and that switches to the high state if no IRE pulse is delivered in 3.5 seconds—the synchronization module communicates changes in the Sync Problem state to the graphic user interface—and if the Sync Problem is high for 12 seconds the software aborts treatment, 6) Sync Condition—(Synchronization Condition) is an internal indicator in the memory of the control device 1 that is normally in the low state and that switches to high when the control device 1 receives a synchronization signal during a blanking period—and switches back to low when a synchronization signal is received outside of a blanking period, 7) Sync Status is a message displayed on the NanoKnife® (or other energy delivery device) display by the graphic interface user depending on the state of the Sync Problem indicator and the Sync Condition indicator.

Figure 15:
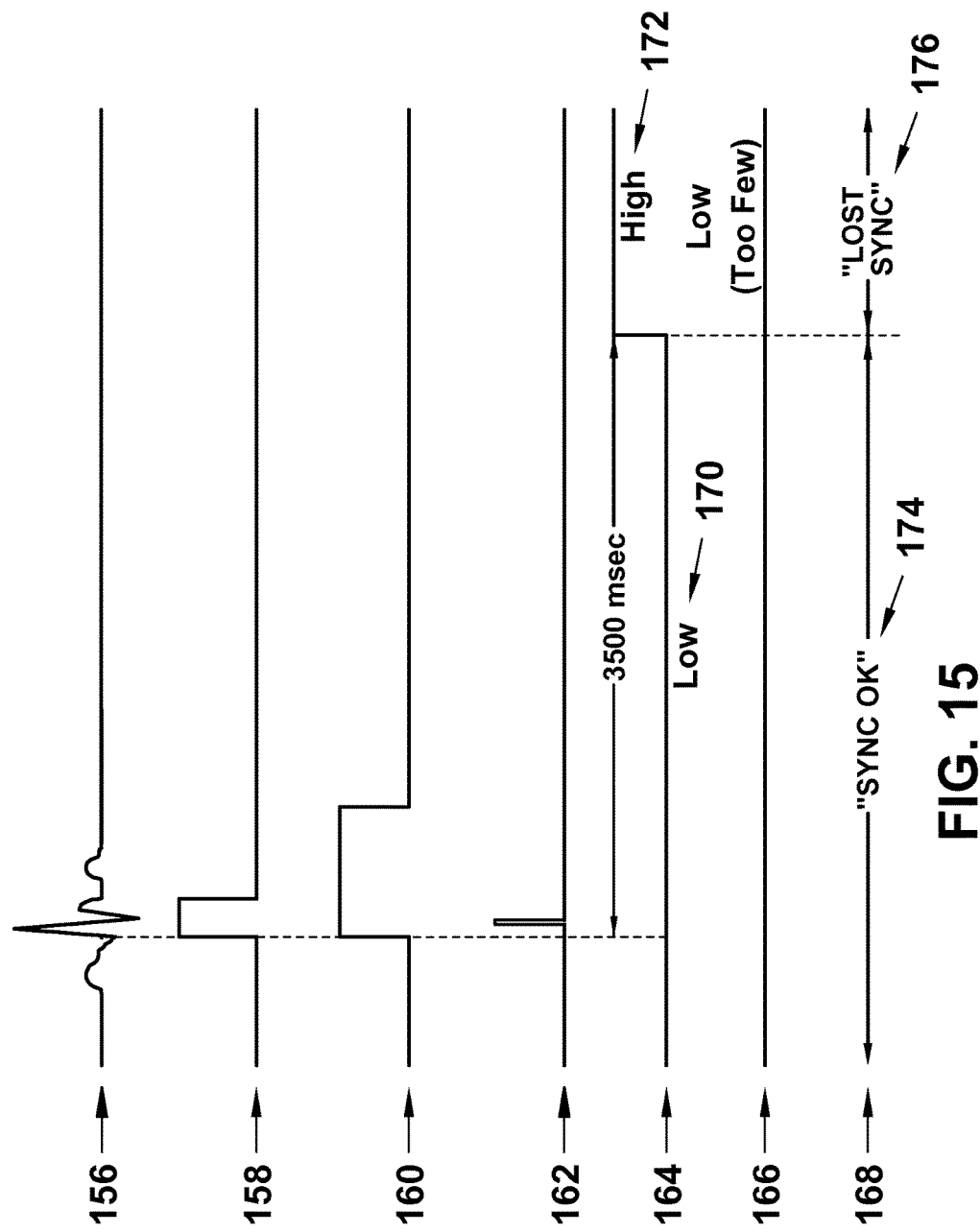
FIG. 15 indicates waveforms of timing diagrams indicating how the synchronization condition and synchronization problem indicators change in relation to various cardiac rhythms, most specifically referring to a lost synchronization condition.

Referring now to FIG. 15, this shows waveforms for Cardiac 156, Accusync 168, Blanking 160, Treatment 162, Sync Problem 164, and Sync Condition 166, and Sync Status 168. FIG. 15 shows an example of lost synchronization. There is a single electrical signal for a cardiac rhythm shown, and then it stops. There is one Accusync signal released 158 and one IRE energy pulse release 162. The Sync Problem level starts at a low setting 170, and after 3.5 seconds the Sync Problem setting changes to high 172. The Sync Status 168 changes from "Sync OK" 174 to "Sync Lost" 176 or otherwise indicates the change graphically.

Figure 16:
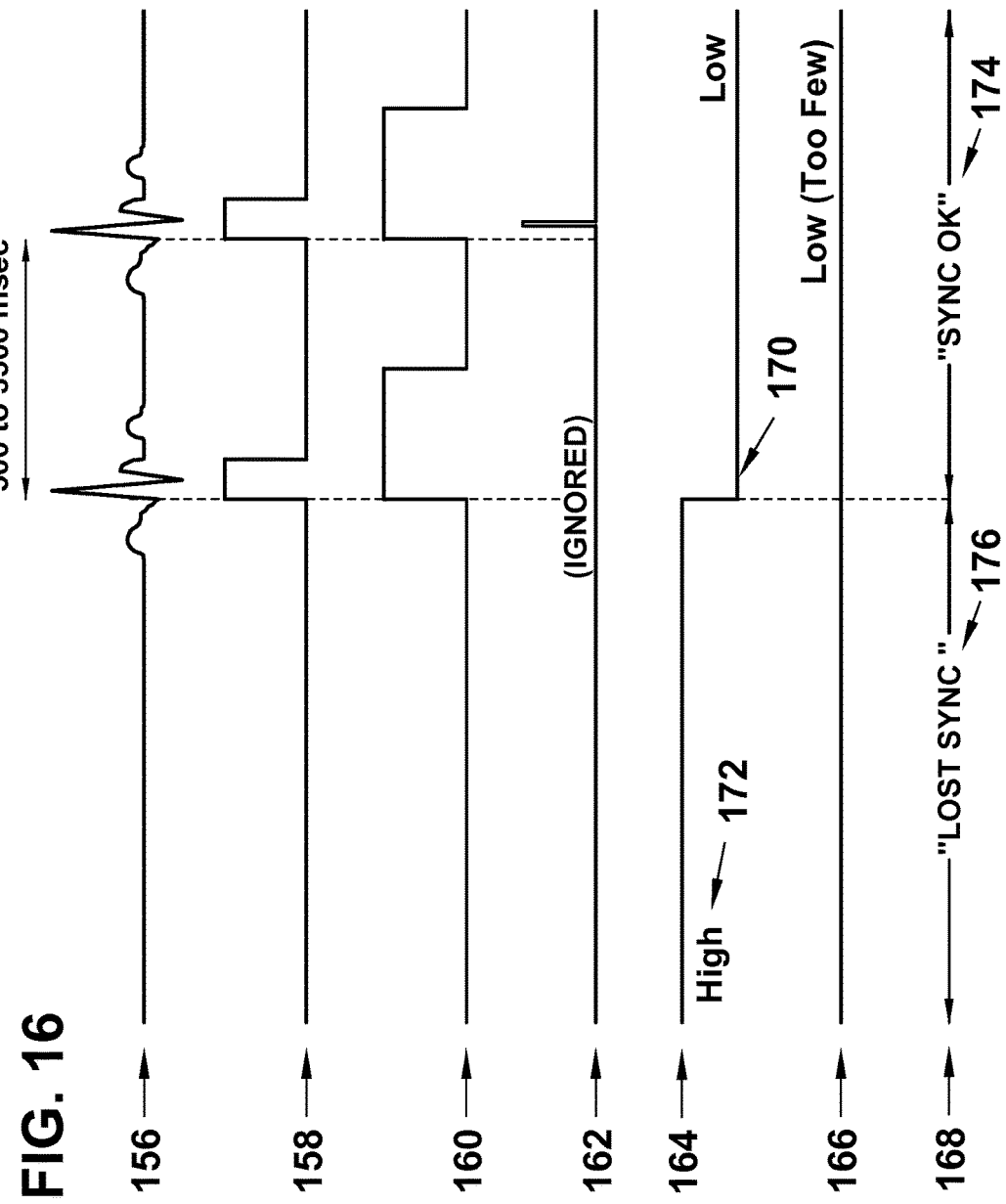
FIG. 16 indicates waveforms of timing diagrams indicating how the synchronization condition and synchronization problem indicators change in relation to various cardiac rhythms, most specifically referring to recovery from a lost synchronization condition.

FIG. 16 shows waveforms for a lost synchronization recovery. A Cardiac signal returns 156, and the Sync Problem level fans from high 172 to low 170. The Sync Status output changes back from "Sync Lost" 176 to "Sync OK" 174.

Figure 17:
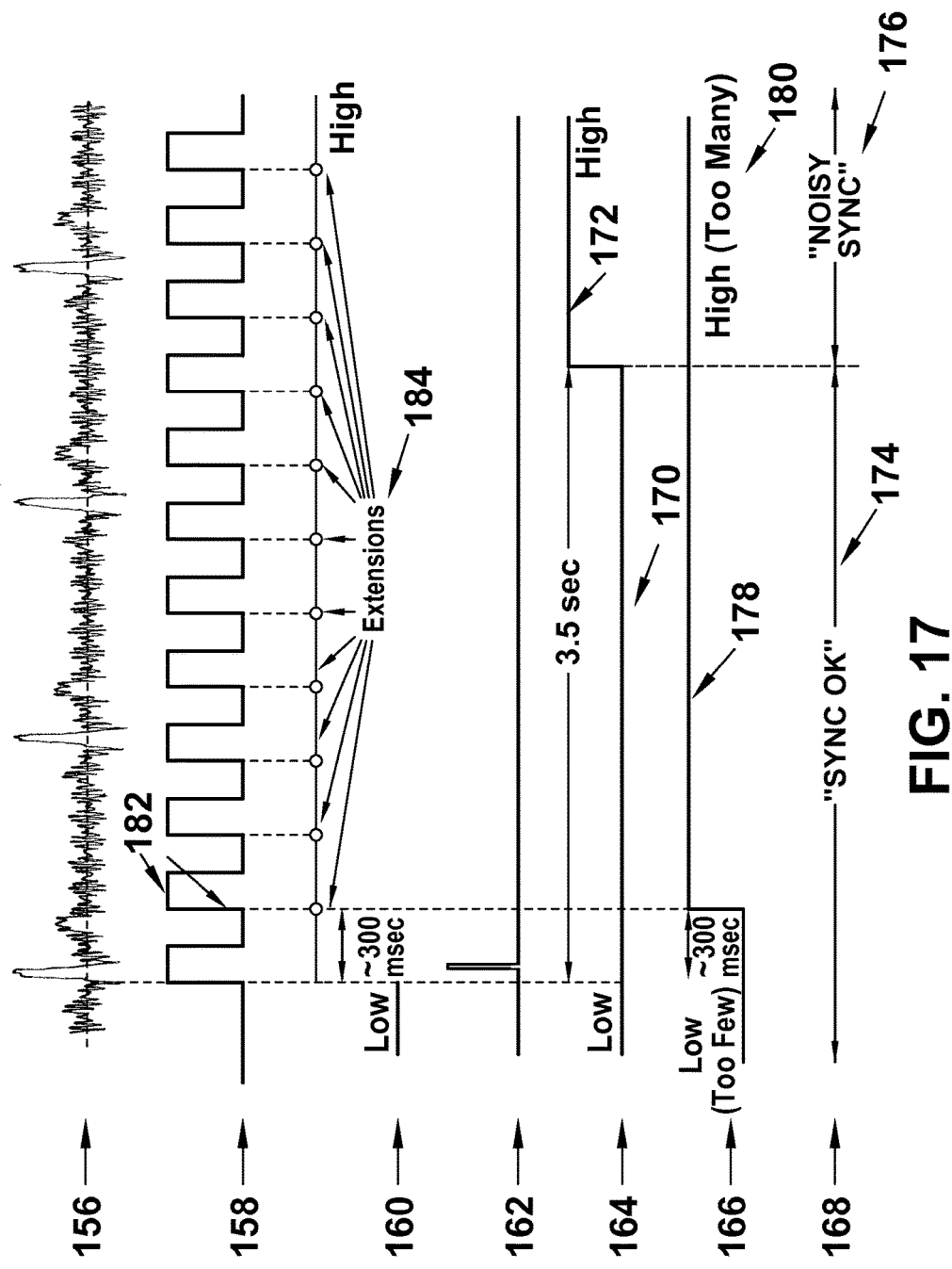
FIG. 17 indicates waveforms of timing diagrams indicating how the synchronization condition and synchronization problem indicators change in relation to various cardiac rhythms, most specifically referring to output change in a noisy signal condition.

FIG. 17 shows waveforms for how the Sync Problem 164, Sync Condition 166, and Sync Status 168 outputs change in a noisy signal condition. First, a lot of noise can be seen in the Cardiac electrical rhythm 156. The synchronization signal (Accusync, 158) output shows that synchronization pulses are received within the blanking periods 182. There are Blanking periods 160 and extensions in response 184. One IRE pulse (treatment, 162) is delivered and that is all. The Sync Problem 164 level changes from low 170 to high 172 after 3.5 seconds. The Sync Condition 166 level changes from low 178 to high 180. The Sync Status 168 output changes from "Sync OK" 174 to "Noisy Sync" 176 or some equivalent graphical display.

FIG. 18 shows waveforms for recovery from a noisy signal condition. The Cardiac electrical signal output 156 changes from noisy (aberrant) 190 to normal 192. The Accusync output 158 changes from signals within the blanking range 182 to the normal signals 188 as the cardiac rhythm returns to normal. The blanking periods 160 that were being extended 184 return to the normal 500 ms blanking times with gaps between 194. The IRE energy pulse release (treatment, 162) returns 198, with the first Accusync signal being ignored 196 (and with there being a release on the second normal Accusync signal). The Sync Problem indicator 164 changes from high 172 to low 170 as the normal cardiac rhythm returns. The Sync Condition indicator 166 changes from high 180 to low 186, and the Sync Status 168 output moves from "Noisy Sync" 176 to "Sync OK" 174.

FIG. 19 indicates waveforms for output that shows a situation where due to a T wave abnormality, the T wave is counted twice by the synchronization signaling device (Accusync) so a second synchronization signal is indicated. The Cardiac electrical signal output 156 shows an aberration near the T wave 200. As a result, there is a second synchronization signal (Accusync output 158) within the blanking period 182, and the blanking period (line 160) is extended 184 to account for this. The Sync Condition indicator (line 166) moves from low 186 to high 180 and then returns to low once the normal synchronization signal is received. In this example treatment can continue and the Sync Status 166 remains as "Sync OK" 174 throughout. Treatment line 162 is shown for completeness.

Figure 20A:
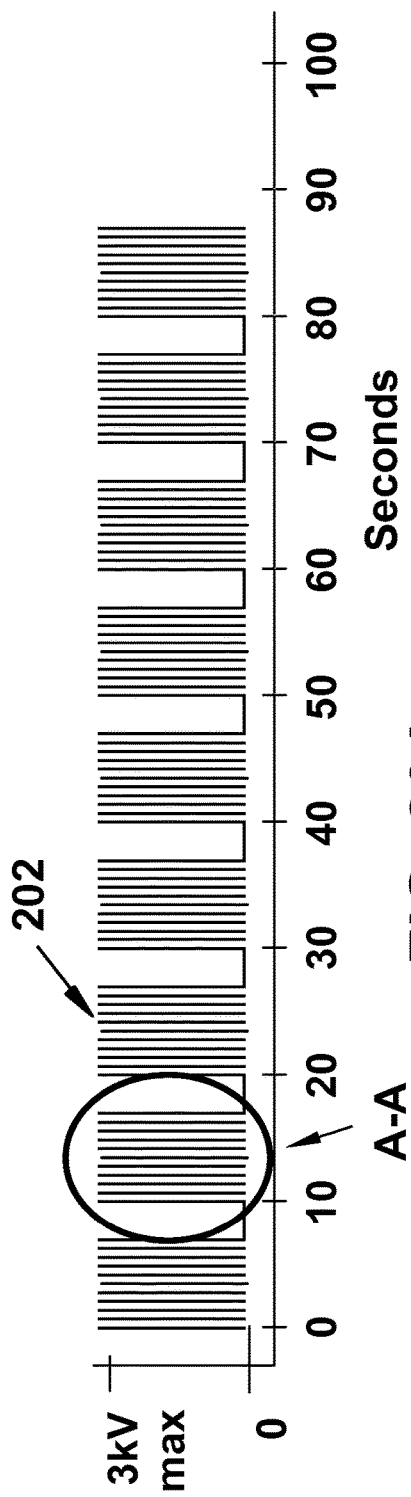
FIGS. 20A-B show a chart and expanded view of indicating a specific mode (mode 2) of IRE energy pulse delivery contemplated for the current invention.
Figure 20B:
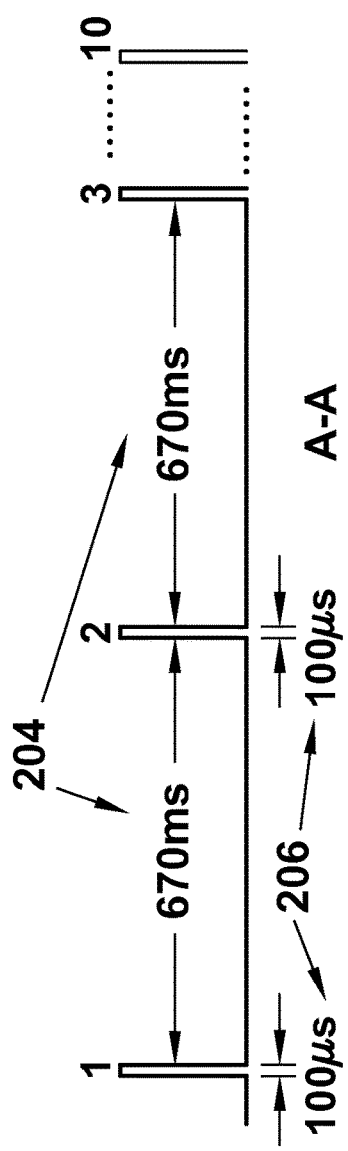

FIGS. 20A-B and 21A-B indicate waveforms that show two examples of modes of IRE delivery discussed in Table 1. FIG. 20 shows mode 2 (FIG. 20B is an expanded view of part of FIG. 20A) and FIG. 21 shows mode 3 (FIG. 21B is an expanded view of FIG. 21A). In FIG. 20, there are 90 pulses of 100 microseconds (100 microseconds for each pulse 206), 670 milliseconds between pulses 204, with a delivery rate of 90 pulses per minute, delivered in trains of 10 pulses 202, with 3500 milliseconds between trains. In FIG. 21 showing mode 3, there are 90 pulses of 100 microseconds (100 microseconds for each pulse 206), 250 milliseconds between pulses 208, with a delivery rate of 240 pulses per minute, delivered in trains of 10 pulses 202, with 3500 milliseconds between trains.

While the embodiments shown use IRE pulses as treatment energy signals, persons of ordinary skill in the art will appreciate that the present invention can work with any other treatment energy signals and may work particularly well for treatment signals that may potentially affect the heart beat or signal processing in a cardiac device that generates synchronization signals.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed:

1. A system for synchronizing application of treatment signals with a cardiac rhythm, comprising:
    a cardiac device that receives a first synchronization signal indicating that a patient is in a predetermined phase of a cardiac rhythm; and
    a synchronization module coupled to the cardiac device to receive the first synchronization signal, a blanking period beginning after receiving the first synchronization signal, the synchronization module operable to automatically extend the blanking period the moment a second synchronization signal is received during the blanking period, the synchronization module automatically extends the blanking period from the time the second synchronization signal is received without ever stopping the blanking period to prevent the treatment signal from being applied to the patient during the extended blanking period.

2. The system of claim 1, wherein the synchronization module is operable to dynamically extend the blanking period when a new synchronization signal is received before the blanking period expires.

3. The system of claim 1, wherein the synchronization module is operable to:
    start a blanking period after receiving the synchronization signal;
    control a medical treatment device to apply a first treatment signal; and
    once the first treatment signal has been applied, prevent the medical treatment device from applying a subsequent treatment signal within the blanking period.

4. The system of claim 1, wherein the synchronization module is operable to start a new blanking period when a subsequent synchronization signal is received by the cardiac device after the blanking period.

5. The system of claim 1, wherein the synchronization module is operable to:
    start a new blanking period when a subsequent synchronization signal is received after the blanking period;
    control a medical treatment device to apply a first treatment signal; and
    prevent the medical treatment device from applying a subsequent treatment signal within the new blanking period.

6. The system of claim 1, wherein the synchronization module, after receiving the synchronization signal, controls a medical treatment device to apply a first treatment signal after waiting a predetermined time period from the receipt of the synchronization signal.

7. The system of claim 6, wherein the synchronization module controls the medical treatment device to apply at least one IRE pulse as the first treatment signal.

8. The system of claim 1, wherein the synchronization module receives the synchronization signal for each occurrence of an R-wave from the cardiac device.

9. The system of claim 1, wherein the synchronization module is operable to:
    start a blanking period after receiving the synchronization signal;
    control a medical treatment device to apply a first treatment signal;
    once the first treatment signal has been applied, prevent the medical treatment device from applying a subsequent treatment signal within the blanking period;
    dynamically extend the blanking period when a new synchronization signal is received within the blanking period.

10. A system for synchronizing application of treatment signals with a cardiac rhythm, comprising:
    a cardiac device that continuously generates a first synchronization signal indicating that a patient is in a predetermined phase of a cardiac rhythm; and
    a synchronization module coupled to the cardiac device to receive the first synchronization signal, a blanking period beginning after receiving the first synchronization signal and operable to automatically extend the blanking period when a second synchronization signal is received during the blanking period to prevent the treatment signal from being applied to the patient during the blanking period, resulting in a continuous blanking period of between 560-800 milliseconds.

11. The system of claim 10, wherein:
the cardiac device receive the synchronization signal which indicates that a T-wave phase of a cardiac rhythm of a patient has started; and
the synchronization module prevents the medical treatment device from applying a treatment signal during the blanking period.

12. The system of claim 10, wherein, based on the received synchronization signal, the synchronization module dynamically adjusts the blanking period during which an application of the treatment signal to the patient by the medical treatment device is prevented.

13. The system of claim 10, wherein the synchronization module is operable to:
start the blanking period after receiving the synchronization signal;
control the medical treatment device to apply a first treatment signal after receiving the synchronization signal; and
once the first treatment signal has been applied, prevent the medical treatment device from applying a subsequent treatment signal within the blanking period.

14. The system of claim 10, wherein:
the synchronization module, after receiving the synchronization signal, controls the medical treatment device to apply at least one IRE pulse as the first treatment signal after waiting a predetermined time period from the receipt of the synchronization signal.

15. The system of claim 10, wherein the synchronization module is operable to:
start a blanking period after receiving the synchronization signal;
control the medical treatment device to apply a first treatment signal;
once the first treatment signal has been applied, prevent the medical treatment device from applying a subsequent treatment signal within the blanking period;
dynamically extend the blanking period when a new synchronization signal is received within the blanking period.

16. A system for synchronizing application of treatment signals with a cardiac rhythm, comprising:
a cardiac device that continuously generates a first synchronization signal indicating that a patient is in a predetermined phase of a cardiac rhythm; and
an energy delivery control device that continuously receives the first synchronization signal from the cardiac device, a blanking period beginning after receiving the first synchronization signal, the energy delivery control device operable to automatically extend the blanking period when a second synchronization signal is received during the blanking period before the blanking period ends to prevent the treatment signal from being applied to the patient during the blanking period, wherein both the cardiac device and the energy delivery control device are both external to the patient's body.

* * * * *